United States Patent
Wissner et al.

(10) Patent No.: US 6,821,988 B2
(45) Date of Patent: Nov. 23, 2004

(54) 3-CYANOQUINOLINES AS INHIBITORS OF EGF-R AND HER2 KINASES

(75) Inventors: Allan Wissner, Ardsley, NY (US); Hwei-Ru Tsou, New City, NY (US); Middleton Brawner Floyd, Jr., Suffern, NY (US); Bernard D. Johnson, Stony Point, NY (US); Elsebe Geraldine Overbeek-Klumpers, DL Baarn (NL)

(73) Assignee: Wyeth Holdings Corporation, Madison, NJ (US)

( * ) Notice: Subject to any disclaimer, the term of this patent is extended or adjusted under 35 U.S.C. 154(b) by 0 days.

(21) Appl. No.: 10/305,438

(22) Filed: Nov. 26, 2002

(65) Prior Publication Data

US 2003/0149056 A1 Aug. 7, 2003

Related U.S. Application Data

(60) Provisional application No. 60/333,568, filed on Nov. 27, 2001.

(51) Int. Cl.$^7$ ................. A61K 31/47; C07D 215/44; C07D 215/54
(52) U.S. Cl. ............... 514/313; 546/160; 546/153; 546/152; 514/314; 514/312; 514/311
(58) Field of Search ................. 514/313, 311, 514/312, 314; 546/160, 153, 152

(56) References Cited

U.S. PATENT DOCUMENTS 6,002,008 A  12/1999  Wissner et al.

FOREIGN PATENT DOCUMENTS

| WO | WO98/43960 | 10/1998 |
| WO | WO00/18740 | 4/2000 |
| WO | WO00/18761 | 4/2000 |
| WO | WO 01/47892 A1 | 7/2001 |
| WO | WO 02/44166 A1 | 6/2002 |

OTHER PUBLICATIONS

Slamon, D.J., et al.; Science, 235, 177–182 (1987).
Macias, A., et al., Anticancer Res., 7, 459 (1987).
Slamon, D.J., et al.; Science, 244, 707 (1989).
Larock, Richard C.; Comprehensive Organic Transformers, VCH Publishers, 411–415, 1989.
Skehan, P.; Storneg, R.; Scudiero, D.; Monks, A.; McMahon, J.; Vistica, D.; Warren, J.; Bokesch, H.; Kenny, S.; Boyd, M.; New Colorimetric Cytotoxic Assay for Anticancer–Drug Screening; J. Natl. Cancer Inst., 1990, 82, 1107–1112.
Gullick, W.J.; Brit. Med. Bull., 47, 87 (1991).
Reiss, M., et al.; Cancer Res., 51, 6254 (1991).
Burke, T.R.; Drugs Future, 17, 119 (1992).
Chang, C.J.; Geahlen, R.L.; J. Nat. Prod., 55, 1529 (1992).
Lfe, R.; J. Med. Chem, 35(18), 3413 (1992).
Parsons, J.T.; Parsons, S.J.; Important Advances in Oncology, DeVita, V.T. ed., J.B. Lippincoll Co., Phila., 3 (1993).
Wilks, A.F.; Cancer Res., 60, 43 (1003), 1993.
Wilson, P.D., et al; Eur. J. Cell Biol., 61(1), 131 (1993).
Nauta, J. et al.; Pediatric Research, 37(6), 755 (1995).
Du J.; Wilson, P.D.; Amer. J. Physiol. 269(2 Pt 1) 487 (1995).
Gattone, V.H., et al.; Developmental Biology, 169(2) 504 (1995).

Primary Examiner—Charanjit S. Aulakh
(74) Attorney, Agent, or Firm—Joy S. Goudie

(57) ABSTRACT

This invention provides compounds of Formula (I), represented by the structure

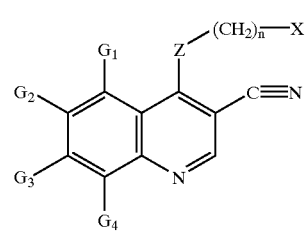

wherein $G_1$, $G_2$, $G_3$, $G_4$, Z, X and n are defined herein, or a pharmaceutically acceptable salt thereof which are useful as antineoplastic agents and in the treatment of polycystic kidney disease.

19 Claims, No Drawings

3-CYANOQUINOLINES AS INHIBITORS OF EGF-R AND HER2 KINASES

CROSS REFERENCE TO RELATED APPLICATIONS

"This application claims priority from copending provisional application Ser. No. 60/333,568 filed on Nov. 27, 2001 the entire disclosure of which is hereby incorporated by reference."

FIELD OF THE INVENTION

This invention relates to certain substituted 3-cyanoquinoline compounds as well as the pharmaceutically acceptable salts thereof. The compounds of the present invention inhibit the action of certain growth factor receptor protein tyrosine kinases (PTK) and other protein kinases thereby inhibiting the abnormal growth of certain cell types. The compounds of this invention are therefore useful for the treatment of certain diseases that are the result of deregulation of these PTKs. The compounds of this invention are anti-cancer agents and are useful for the treatment of cancer in mammals. In addition, the compounds of this invention are useful for the treatment of polycystic kidney disease in mammals. This invention also relates to the manufacture of said 3-cyanoquinolines, their use for the treatment of cancer and polycystic kidney disease, and the pharmaceutical preparations containing them.

BACKGROUND OF THE INVENTION

Protein tyrosine kinases are a class of enzymes that catalyze the transfer of a phosphate group from ATP to a tyrosine residue located on a protein substrate. Protein tyrosine kinases clearly play a role in normal cell growth. Many of the growth factor receptor proteins function as tyrosine kinases and it is by this process that they effect signaling. The interaction of growth factors with these receptors is a necessary event in normal regulation of cell growth. However, under certain conditions, as a result of either mutation or overexpression, these receptors can become deregulated. The result of this is uncontrolled cell proliferation which can lead to tumor growth and ultimately to the disease known as cancer [Wilks A. F., *Adv. Cancer Res.*, 60, 43 (1993) and Parsons, J. T.; Parsons, S. J., *Important Advances in Oncology*, DeVita V. T. Ed., J. B. Lippincott Co., Phila., 3 (1993)]. Among the growth factor receptor kinases and their proto-oncogenes that have been identified and which are targets of the compounds of this invention are the epidermal growth factor receptor kinase (EGF-R kinase, the protein product of the erbB oncogene), and the product produced by the Her2 (also referred to as the neu or erbB-2) oncogene. Since the phosphorylation event is a necessary signal for cell division to occur and since overexpressed or mutated kinases have been associated with cancer, an inhibitor of this event, a protein tyrosine kinase inhibitor, will have therapeutic value for the treatment of cancer and other diseases characterized by uncontrolled or abnormal cell growth. For example, overexpression of the receptor kinase product of the Her2 oncogene has been associated with human breast and ovarian cancers [Slamon, D. J., et. al., *Science*, 244, 707 (1989) and *Science*, 235, 1146 (1987)]. Deregulation of EGF-R kinase has been associated with epidermoid tumors [Reiss, M., et. al., *Cancer Res.*, 51, 6254 (1991)], breast tumors [Macias, A., et. al., *Anticancer Res.*, 7, 459 (1987)], and tumors involving other major organs [Gullick, W. J., *Brit. Med. Bull.*, 47, 87 (1991)]. Because of the importance of the role played by deregulated receptor kinases in the pathogenesis of cancer, many recent studies have dealt with the development of specific PTK inhibitors as potential anti-cancer therapeutic agents [some recent reviews: Burke, T. R., *Drugs Future*, 17, 119 (1992) and Chang, C. J.; Geahlen, R. L., *J. Nat. Prod.*, 55, 1529 (1992)]. The compounds of this invention inhibit the kinase activity of EGF-R and Her2 and are therefore useful for treating certain disease states, such as cancer, that result, at least in part, from deregulation of these receptors. The compounds of this invention are also useful for the treatment and prevention of certain pre-cancerous conditions, such as the growth of colon polyps, that result, at least in part, from deregulation of these receptors.

It is also known that deregulation of EGF receptors is a factor in the growth of epithelial cysts in the disease described as polycystic kidney disease [Du J., Wilson P. D., *Amer. J. Physiol.*, 269(2 Pt 1), 487 (1995); Nauta, J., et al., *Pediatric Research*, 37(6), 755 (1995); Gattone, V. H., et al., *Developmental. Biology*, 169(2), 504 (1995); Wilson, P. D., et al., *Eur. J. Cell Biol.*, 61(1), 131,(1993)]. The compounds of this invention, which inhibit the catalytic function of the EGF receptors, are consequently useful for the treatment of this disease.

Some 3-cyanoquinoline derivatives are inhibitors of tyrosine kinases and are described in the application WO9843960 (U.S. Pat. No. 6,002,008). These 3-cyanoquinolines may be substituted at carbon-5 through carbon-8 with an unsubstituted phenyl, alkene or alkyne group. Applications WO0018761 and WO0018740 also describe 3-cyanoquinoline inhibitors. A 3-cyanoquinoline with a 4-(2-methylanilino) substituent having gastric ($H^+$/$K^+$)-ATPase inhibitory activity at high concentrations has been described [Ife, R., *J. Med. Chem.*, 35(18), 3413 (1992)].

The compounds of the present invention are 3-cyanoquinolines which inhibit the activity of protein kinases that are required for cell growth and differentiation and are therefore useful for the treatment of certain diseases that result from activity of these protein kinases. In particular, the compounds of this invention inhibit the kinase activity of EGF-R and Her2 kinases. The compounds of this invention are anti-cancer agents and are useful for the treatment of cancer in mammals. Further, the compounds of this invention are useful for the treatment of polycystic kidney disease in mammals.

SUMMARY OF THE INVENTION

In accordance with the present invention, there is provided compounds represented by Formula (I):

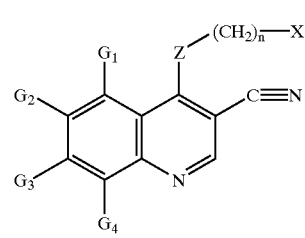

wherein:
Z is —NH—, —O—, —S—, or —NR—;
R is alkyl of 1 to 6 carbon atoms, or carboalkyl of 2 to 7 carbon atoms;
X is cycloalkyl of 3 to 7 carbon atoms, which may be optionally substituted with one or more alkyl groups of 1 to 6 carbon atoms; or X is pyridinyl, pyrimidinyl, or aryl and may optionally be mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is a bicyclic aryl or bicyclic heteroaryl ring system of 8 to 12 atoms, where the bicyclic heteroaryl ring contains 1 to 4 heteroatoms independently selected from N, O, and S; wherein the bicyclic aryl or bicyclic heteroaryl ring may be optionally mono-, di-, tri-, or tetra-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy ($C_6H_5$S—), benzoyl, benzyl, amino, alkylamino of 1 to 6,carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or X is the radical

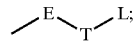

E is pyridinyl, pyrimidinyl, or aryl optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

T is substituted on E at carbon and is —NH(CH$_2$)$_m$—, —O(CH$_2$)$_m$—, —S(CH$_2$)$_m$—, —NR(CH$_2$)$_m$—, —(CH$_2$)$_m$— —(CH$_2$)$_m$NH—, —(CH$_2$)$_m$O—, —(CH$_2$)$_m$S—, or —(CH$_2$)$_m$NR—;

L is an aryl ring optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy ($C_6H_5$S—), benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

Pyridinyl, pyrimidinyl, or aryl are pyridinyl, pyrimidinyl, or aryl radicals, respectively, optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkylC$_1$–C$_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzoylamino;

$G_1$, $G_2$, $G_3$, and $G_4$ are each, independently, hydrogen, halogen, alkyl of 1 to 6 carbon atoms, alkenyl of 2 to 6 carbon atoms, alkynyl of 2 to 6 carbon atoms, alkenyloxy of 2 to 6 carbon atoms, alkynyloxy of 2 to 6 carbon atoms, hydroxymethyl, halomethyl, alkanoyloxy of 2 to 6 carbon atoms, alkenoyloxy of 3 to 8 carbon atoms, alkynoyloxy of 3 to 8 carbon atoms, alkanoyloxymethyl of 2 to 7 carbon atoms, alkenoyloxymethyl of 4 to 9 carbon atoms, alkynoyloxymethyl of 4 to 9 carbon atoms, alkoxymethyl of 2 to 7 carbon atoms, alkoxy of 1 to 6 carbon atoms, alkylthio of 1 to 6 carbon atoms (alkylC$_1$–C$_6$)S—, alkylsulphinyl of 1 to 6 carbon atoms, alkylsulphonyl of 1 to 6 carbon atoms, alkylsulfonamido of 1 to 6 carbon atoms, alkenylsulfonamido of 2 to 6 carbon atoms, alkynylsulfonamido of 2 to 6 carbon atoms, hydroxy, trifluoromethyl, trifluoromethoxy, cyano, nitro, carboxy, carboalkoxy of 2 to 7 carbon atoms, carboalkyl of 2 to 7 carbon atoms, phenoxy, phenyl, thiophenoxy (C$_6$H$_5$S—), benzyl, amino, hydroxyamino, alkoxyamino of 1 to 4 carbon atoms, alkylamino of 1 to 6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6 to 12 carbon atoms, phenylamino, benzylamino, R$_2$NH,

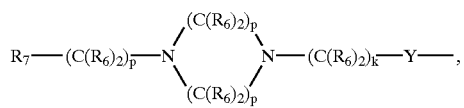

R$_8$R$_9$—CH—M—(C(R$_6$)$_2$)$_k$—Y—,
R$_7$—(C(R$_6$)$_2$)$_g$—Y—, R$_7$—(C(R$_6$)$_2$)$_p$—M—(C(R$_6$)$_2$)$_k$—Y—, or Het-(C(R$_6$)$_2$)$_q$—W—(C(R$_6$)$_2$)$_k$—Y—, provided that either G$_2$ or G$_3$ or both G$_2$ and G$_3$ are R$_2$NH;

Y is a divalent radical selected from the group consisting of

—S—, —(CH$_2$)$_a$—, —O—, and —N(R$_6$)—;

R$_7$ is —NR$_6$R$_6$, —OR$_6$, —J, —N(R$_6$)$_3$ $^+$Q$^-$, or —NR$_6$(OR$_6$);

M is >NR$_6$, —O—, >N—(C(R$_6$)$_2$)$_p$NR$_6$R$_6$, or >N—(C(R$_6$)$_2$)$_p$—OR$_6$;

W is >NR$_6$, —O— or is a bond;

Het is a heterocyclic radical selected from the group consisting of morpholine, thiomorpholine, thiomorpholine S-oxide, thiomorpholine S,S-dioxide, piperidine, pyrrolidine, aziridine, pyridine, imidazole, 1,2,3-triazole, 1,2,4-triazole, thiazole, thiazolidine, tetrazole, piperazine, furan, thiophene, tetrahydrothiophene, tetrahydrofuran, dioxane, 1,3-dioxolane, tetrahydropyran, and

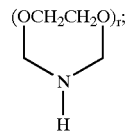

which may be optionally mono- or di-substituted on carbon with R$_6$, hydroxy, —N(R$_6$)$_2$, —OR$_6$, —(C(R$_6$)$_2$)$_s$OR$_6$ or —(C(R$_6$)$_2$)$_s$N(R$_6$)$_2$;

optionally mono-substituted on nitrogen with R$_6$; and optionally mono or di-substituted on a saturated carbon with divalent radicals —O— or —O(C(R$_6$)$_2$)$_s$O—;

R$_6$ is hydrogen, alkyl of 1 to 6 carbon atoms, alkenyl of 2 to 6 carbon atoms, alkynyl of 2 to 6 carbon atoms, cycloalkyl of 3 to 7 carbon atoms, carboalkyl of 2 to 7 carbon atoms, carboxyalkyl 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms (alkylC$_1$–C$_6$)S—, hydroxy, carboxyl, carboalkoxy of 2 to 7 carbon atoms, phenoxy, phenyl, thiophenoxy (C$_6$H$_5$S—), benzoyl, benzyl, phenylamino, benzylamino, alkanoylamino of 1 to 6 carbon atoms, or alkyl of 1 to 6 carbon atoms; provided that the alkenyl or alkynyl moiety is bound to a nitrogen or oxygen atom through a saturated carbon atom;

R$_2$, is selected from the group consisting of

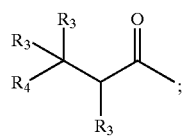

R$_3$ is hydrogen, alkyl of 1 to 6 carbon atoms, carboxy, carboalkoxy of 1 to 6 carbon atoms, phenyl, carboalkyl of 2 to 7 carbon atoms,

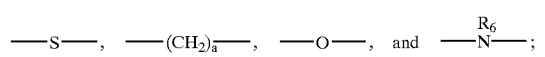

R$_7$—(C(R$_6$)$_2$)$_s$—, R$_7$—(C(R$_6$)$_2$)$_p$—M—(C(R$_6$)$_2$)$_r$—, R$_8$R$_9$—CH—M—(C(R$_6$)$_2$)$_r$—, or Het-(C(R$_6$)$_2$)$_q$—W—(C(R$_6$)$_2$)$_r$—;

R$_4$ is —NR$_6$R$_6$, —OR$_6$, —SR$_6$, R$_7$—(C(R$_6$)$_2$)$_p$—S—, R$_7$—(C(R$_6$)$_2$)$_p$—N(R$_6$)—, R$_7$—(C(R$_6$)$_2$)$_p$—O—, R$_8$R$_9$—CH—N(R$_6$)—, R$_8$R$_9$—CH—S—, R$_8$R$_9$—CH—O—, Het-(C(R$_6$)$_2$)$_q$—N(R$_6$)—, Het-(C(R$_6$)$_2$)$_q$—S—, Het-(C(R$_6$)$_2$)$_q$—O—,

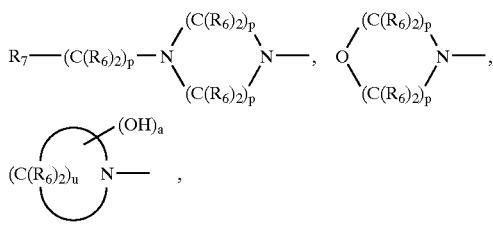
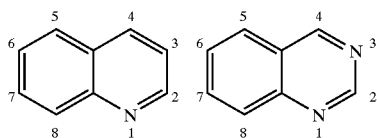

cysteine, or a peptide comprised of 2 to 10 native amino acid residues containing at least one unoxidized cysteine residue wherein $R_4$ is bound to the rest of the molecule through the sulfur atom of one or more of the cysteine residues;

$R_8$ and $R_9$ are each, independently, —$(C(R_6)_2)_rNR_6R_6$, or —$(C(R_6)2)_rOR_6$;

J is independently hydrogen, chlorine, fluorine, or bromine;

a is an integer of 0–1;

g is an integer of 1–6;

k is an integer of 0–4;

n is an integer of 0–1;

m is an integer of 0–3;

p is an integer of 2–4;

q is an integer of 0–4;

r is an integer of 1–4;

s is an integer of 1–6 u is an integer of 2–6;

$Q^-$ is a counterion selected from salts formed from organic and inorganic acids;

provided that:
  a. when $R_6$ is alkenyl of 2 to 7 carbon atoms or alkynyl of 2 to 7 carbon atoms, such alkenyl or alkynyl moiety is bound to a nitrogen or oxygen atom through a saturated carbon atom;
  b. when Y is —$NR_6$— and $R_7$ is —$NR_6R_6$, —$N(R_6)_3$ $^+Q^-$, or —$NR_6(OR_6)$, then g is an integer of 2 to 6;
  c. when M is —O— and $R_7$ is —$OR_6$ then p is an integer of 1 to 4;
  d. when Y is —$NR_6$— then k is an integer of 2 to 4;
  e. when Y is —O— and M or W is —O— then k is an integer of 1 to 4;
  f. when W is not a bond with Het bonded through a nitrogen atom then q is an integer of 2 to 4 and when W is a bond with Het bonded through a nitrogen atom and Y is —O— or —$NR_6$— then k is an integer of 2 to 4;

or a pharmaceutically acceptable salt thereof.

DESCRIPTION OF THE PREFERRED EMBODIMENTS

The compounds of this invention are certain substituted 3-cyanoquinolines. Throughout this patent application, the quinoline and quinazoline ring systems will be numbered as indicated in the formulas below.

Preferred bicyclic aryl or bicyclic heteroaryl ring systems include naphthalene, 1,2,3,4-tetrahydronaphthalene, tetralin, indane, 1-oxo-indane, 1,2,3,4-tetrahydroquinoline, naphthyridine, benzofuran, 3-oxo-1,3-dihydroisobenzofuran, benzothiaphene, 1,1-dioxobenzothiaphene, indole, 2,3-dihydroindole, 1,3-dioxo-2,3-dihydro-1H-isoindole, benzotriazole, 1H-indazole, indoline, benzopyrazole, 1,3-benzodioxole, benzoxazole, purine, phthalimide, coumarin, chromone, quinoline, terahydroquinoline, isoquinoline, benzimidazole, quinazoline, pyrido[2,3-b]pyridine, pyrido[3,4-b]pyrazine, pyrido[3,2-c]pyridazine, pyrido[3,4-b]pyridine, 1H-pyrazole[3,4-d]pyrimidine, 1,4-benzodioxane, pteridine, 2(1H)-quinolone, 1(2H)-isoquinolone, 2-oxo-2,3-dihydrobenzthiazole, 1,2-methylenedioxybenzene, 2-oxindole, 1,4-benzisoxazine, benzothiazole, quinoxaline, quinoline-N-oxide, isoquinoline-N-oxide, quinoxaline-N-oxide, quinazoline-N-oxide, benzazine, phthalazine, 1,4-dioxo-1,2,3,4-tetrahydrophthalazine, 2-oxo-1,2-dihydroquinoline, 2,4-dioxo-1,4-dihydro-2H-benzo[d][1,3]oxazine, 2,5-dioxo-2,3,4,5-tetrahydro-1H-benzo[e][1,4]diazepine, or cinnoline.

A preferred cysteine containing peptide is glutathione.

When L is a 5 or 6-membered heteroaryl ring, preferred heteroaryl rings include pyridine, pyrimidine, imidazole, thiazole, thiazolidine, pyrrole, furan, thiophene, oxazole, or 1,2,4-triazole.

Either or both rings of the bicyclic aryl or bicyclic heteroaryl group may be fully unsaturated, partially saturated, or fully saturated. An oxo substituent on the bicyclic aryl or bicyclic heteroaryl moiety means that one of the carbon atoms has a carbonyl group. A thio substituent on the bicyclic aryl or bicyclic heteroaryl moiety means that one of the carbon atoms has a thiocarbonyl group. When a compound of this invention contains a moiety which contains a heteroaryl ring, such heteroaryl ring does not contain O—O, S—S, or S—O bonds in the ring.

When L is a 5 or 6-membered heteroaryl ring, it may be fully unsaturated, partially saturated, or fully saturated. The heteroaryl ring can be bound to T via carbon or nitrogen. An oxo substituent on the heteroaryl ring means that one of the carbon atoms has a carbonyl group. A thio substituent on the heteroaryl ring means that one of the carbon atoms has a thiocarbonyl group.

The alkyl portion of the alkyl, alkoxy, alkanoyloxy, alkoxymethyl, alkanoyloxymethyl, alkylsulphinyl, alkylsulphonyl, alkylsulfonamido, carboalkoxy, carboalkyl, carboxyalkyl, carboalkoxyalkyl, alkanoylamino, N-alkylcarbamoyl, N,N-dialkylcarbamoyl, N-alkylaminoalkoxy, and N,N-dialkylaminoalkoxy include both straight chain as well as branched carbon chains of 1 to 6 carbon atoms. The alkenyl portion of the alkenyl, alkenoyloxymethyl, alkenyloxy, alkenylsulfonamido, substituents include both straight chain as well as branched carbon chains of 2 to 6 carbon atoms and one or more sites of unsaturation and all possible configurational isomers. The alkynyl portion of the alkynyl, alkynoyloxymethyl, alkynylsulfonamido, alkynyloxy, substituents include both straight chain as well as branched carbon chains of 2 to 6 carbon atoms and one or more sites of unsaturation. Carboxy is defined as a —CO$_2$H radical. Carboalkoxy of 2 to 7 carbon atoms is defined as a —CO$_2$R" radical, where R" is an alkyl radical of 1 to 6 carbon atoms. Carboxyalkyl is defined as a HO$_2$C—R'"-radical where R'" is a divalent alkyl radical of 1 to 6 carbon atoms. Carboalkoxyalkyl is defined as a R"O$_2$C—R'"-radical where R'" is a divalent alkyl radical and where R" and R'" together have 2 to 7 carbon atoms. Carboalkyl is defined as a —COR" radical, where R" is an alkyl radical of 1 to 6 carbon atoms. Alkanoyloxy is defined as a —OCOR" radical, where R" is an alkyl radical of 1 to 6 carbon atoms. Alkanoyloxymethyl is defined as a R"CO$_2$CH$_2$— radical, where R" is an alkyl radical of 1 to 6 carbon atoms. Alkoxymethyl is defined as a R"OCH$_2$— radical, where R" is an alkyl radical of 1 to 6 carbon atoms. Alkylsulphinyl is defined as a R"SO— radical, where R" is an alkyl radical of 1 to 6 carbon atoms. Alkylsulphonyl is defined as a R"SO$_2$— radical, where R" is an alkyl radical of 1 to 6 carbon atoms. Alkylsulfonamido, alkenylsulfonamido, alkynylsulfonamido are defined as a R"SO$_2$NH— radical, where R" is an alkyl radical of 1 to 6 carbon atoms, an alkenyl radical of 2 to 6 carbon atoms, or an alkynyl radical of 2 to 6 carbon atoms, respectively. N-alkylcarbamoyl is defined as a R"NHCO— radical, where R" is an alkyl radical of 1 to 6 carbon atoms. N,N-dialkylcarbamoyl is defined as a R"R'NCO— radical, where R" is an alkyl radical of 1 to 6 carbon atoms, R' is an alkyl radical of 1 to 6 carbon atoms and R' and R" may be the same or different. When X is substituted, it is preferred that it is mono-, di-, or tri-substituted, with mono- and di-substituted being most preferred. It is preferred that of the substituents G$_1$ and G$_4$, at least one is hydrogen and it is most preferred that both be hydrogen. It is also preferred that X is a phenyl ring optionally substituted, Z is —NH—, and n is an integer of 0.

Het is a heterocycle, as defined above which may be optionally mono- or di-substituted on carbon with R$_6$, optionally mono-substituted on nitrogen with R$_6$, optionally mono- or di-substituted on carbon with hydroxy, —N(R$_6$)$_2$, or —OR$_6$, optionally mono or di-substituted on carbon with —(C(R$_6$)$_2$)$_s$OR$_6$ or —(C(R$_6$)$_2$)$_s$N(R$_6$)$_2$, and optionally mono or di-substituted on a saturated carbon with divalent —O— or —O(C(R$_6$)$_2$)$_s$O— (carbonyl and ketal groups, respectively); in some cases when Het is substituted with —O— (carbonyl), the carbonyl group can be hydrated. Het may be bonded to W when q is an integer of 0 via a carbon atom on the heterocyclic ring, or when Het is a nitrogen containing heterocycle which also contains a saturated carbon-nitrogen bond, such heterocycle may be bonded to carbon, via the nitrogen when W is a bond. When q is an integer of 0 and Het is a nitrogen containing heterocycle which also contains an unsaturated carbon-nitrogen bond, that nitrogen atom of the heterocycle may be bonded to carbon when W is a bond and the resulting heterocycle will bear a positive charge. When Het is substituted with R$_6$, such substitution may be on a ring carbon, or in the case of a nitrogen containing heterocycle, which also contains a saturated carbon-nitrogen bond, such nitrogen may be substituted with R$_6$ or in the case of a nitrogen containing heterocycle, which also contains an unsaturated carbon-nitrogen bond, such nitrogen may be substituted with R$_6$ in which case the heterocycle will bear a positive charge. Preferred heterocycles include pyridine, 2,6-disubstituted morpholine, 2,5-disubstituted thiomorpholine, 2-substituted imidazole, substituted thiazole, N-substituted imidazole, N-subsitituted 1,4-piperazine, N-substituted piperadine, and N-substituted pyrrolidine.

The peptides included among the R$_4$ substituents are comprised of 2 to 10 native amino acid residues containing at least one unoxidized cysteine residue. The N-terminus of these peptides can be acylated with a C$_1$–C$_5$ alkanoyl group and/or the C-terminus can be esterified with a C$_1$–C$_5$ alkoxy group. In those case where there are more than one cysteine residue, each cysteine can optionally be bound to a 3-cyanoquinoline through the sulfur atom.

Preferred compounds of this invention are described below. Except as otherwise indicated below, the substituents are as defined above.

A. Compounds according to Formula (I), wherein Z is —NH—, n is an integer of 0, and X is aryl optionally substituted or a pharmaceutically acceptable salt thereof.

B. Compounds according to Formula (I), wherein Z is —NH—, n is an integer of 0, X is phenyl optionally substituted or a pharmaceutically acceptable salt thereof.

C. Compounds according to Formula (I), wherein Z is —NH—, n is an integer of 0, X is aryl optionally substituted and G$_1$ and G$_4$ are H or a pharmaceutically acceptable salt thereof.

D. Compounds according to Formula (I), wherein Z is —NH—, n is an integer of 0, X is substituted or unsubstituted bicyclic aryl or bicyclic heteroaryl ring system, or a pharmaceutically acceptable salt thereof.

E. Compounds according to Formula (I), wherein Z is —NH—, n is an integer of 0, X is phenyl optionally substituted and G$_1$ and G$_4$ are H or a pharmaceutically acceptable salt thereof.

Specifically preferred compounds of this invention or a pharmaceutically acceptable salt thereof include:

N-(4-{3-chloro-4-[(4-phenyl-1,3-thiazol-2-yl)sulfanyl]anilino}-3-cyano-7-methoxy-6-quinolinyl)-3,4-bis(dimethylamino)-2-butanamide, N-[4-(3-Chloro-4-fluoro-phenylamino)-3-cyano-7-methoxy-quinolin-6-yl]-3,4-bis-(3-hydroxy-pyrrolidin-1-yl)-butyramide, N-[4-(3-Chloro-4-fluoroanilino)-3-cyano-7-ethoxy-6-quinolinyl]-3-(dimethylamino)butanamide, N-{4-[4-(Benzyloxy)-3-chloroanilino]-3-cyano-7-ethoxy-6-quinolinyl}-3,6-bis(dimethylamino)hexanamide, N-{4-[4-(Benzyloxy)-3-chloroanilino]-3-cyano-7-ethoxy-6-quinolinyl}-3,4-di(1-pyrrolidinyl)butanamide, (2R)-2-amino-5-({2-[(carboxymethyl)amino]-1-[({3-{[4-(3-chloro-4-fluoroanilino)-3-cyano-7-ethoxy-6-quinolinyl]amino}-1-[(dimethylamino)methyl]-3-oxopropyl}sulfanyl)methyl]-2-oxoethyl}amino)-5-oxopentanoic acid, and N-{4-[4-(Benzyloxy)-3-chloroanilino]-3-cyano-7-ethoxy-6-quinolinyl}-3,4-bis(dimethylamino)butanamide, or a pharmaceutically acceptable salt thereof.

The compounds of this invention may contain one or more asymmetric carbon atoms; in such cases, the compounds of this invention include the individual diasteromers, the racemates, and the individual R and S entantiomers thereof. Some of the compounds of this invention may contain one or more double bonds; in such cases, the compounds of this invention include each of the possible configurational isomers as well as mixtures of these isomers. When a compound of this invention contains a moiety containing the same substituent more than once (for example, when $R_7$ is —$NR_6R_6$), each substituent ($R_6$ in this example) may be the same or different.

For the compounds of Formula (I) defined above and referred to herein, unless otherwise noted, the following terms are defined:

Halogen, as used herein means chloro, fluoro, bromo and iodo.

Alkyl as used herein means a branched or straight chain having from 1 to 6 carbon atoms. Exemplary alkyl groups include methyl, ethyl, propyl, isopropyl, butyl, isobutyl, t-butyl, pentyl and hexyl optionally substituted with phenyl, phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialkylamino, thioalkyl, alkoxycarbonyl and acyl.

Alkenyl as used herein means a branched or straight chain having from 2 to 6 carbon atoms, the chain containing at least one carbon-carbon double bond and all possible configurational isomers. Alkenyl, may be used synonymously with the term olefin and includes alkylidenes. Exemplary alkenyl groups include ethenyl, propenyl, 1,4-butadienyl, 3-hexen-1-yl and the like optionally substituted with phenyl, phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialkylamino, thioalkyl, alkoxycarbonyl and acyl.

An alkynyl group is defined as straight or branched carbon chain of 2 to 6 carbon atoms that contains at least one carbon-carbon triple bond and includes propynyl and the like optionally substituted with phenyl, phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialkylamino, thioalkyl, alkoxycarbonyl and acyl.

Alkoxy as used herein means an alkyl-O— group in which the alkyl group is as previously described. Exemplary alkoxy groups include methoxy, ethoxy, n-propoxy, i-propoxy, n-butoxy, t-butoxy and polyethers including —O—$(CH_2)_2OCH_3$.

Cycloalkyl as used herein means a simple carbocycle having a saturated ring having from 3 to 7 carbon atoms and more preferably from 3 to 6 carbon atoms optionally substituted with 1 to 3 independently selected alkyl groups of 1 to 6 carbon atoms. Exemplary cycloalkyl rings include cyclopropyl, cyclobutyl, cyclopentyl, cyclohexyl and adamantyl and the like.

Aryl as used herein means a mono or bicyclic aromatic ring having from 6 to 12 carbon atoms. Monocyclic rings preferably have 6 members and bicyclic rings preferably have 8, 9, 10 or 12 membered ring structures. Exemplary aryl groups include phenyl, alpha-naphthyl, beta-naphthyl, indene, and the like independently substituted with one or more substituents and more preferably with 1 to 3 substituents. Phenyl as used herein refers to a 6-membered aromatic ring optionally mono, di or tri-substituted.

Heteroaryl denotes an unsubstituted or optionally substituted monocyclic 5 or 6 membered ring, which contains 1 to 4, or particularly 1 or 2 heteroatoms which may be the same or different. Nitrogen, oxygen and sulfur are the preferred heteroatoms, provided that the heteroaryl does not contain O—O, S—S or S—O bonds. Specific examples include thiophene, furan, pyrrole, pyrazole, imidazole, 1,2,3-triazole, 1,2,4-triazole, tetrazole, thiazole, oxazole, isothiazole, isoxazole, 1,3,4-oxadiazole, 1,2,4-oxadiazole, 1,3,4-thiadiazole, pyridine, pyrimidine, pyrazine, pyridazine and 1,3,5-triazine. The heteroaryl ring may be oxidized when a heteroatom is a nitrogen atom to provide the corresponding N-oxide, including pyridine —N-oxide. The heteroaryl ring may be oxidized on a sulfur atom to provide the corresponding sulfoxide or sulfone, including thiophene-1-oxide. The heterocyclic ring may contain a carbonyl group on one of the carbon atoms, such as 1,3,4-oxadiazol-2-one.

Bicyclic heteroaryl as used herein refers to saturated or partially unsaturated bicyclic fused rings having 8 to 20 ring atoms containing 1 to 4 heteroatoms which may be the same or different independently selected from nitrogen, oxygen and sulfur optionally substituted with 1 to 3 independently selected substituents which may be the same or different provided that the bicyclic heteroaryl does not contain —O—O, S—S or S—O bonds. Specific examples include: indole, 2,3-dihydroindole, 2-indazole, isoindazole, quinoline, isoquinoline, tetrahydroquinoline, benzofuran, benzothiophene, benzimidazole, benzotriazole, benzothiazole, benzoxazole, benzisoxazole, 1,2-benzopyran, cinnoline, phthalazine, quinazoline, 1,8-naphthyridine, pyrido[3,2-b]pyridine, pyrido[3,4-b]pyridine, pyrido[4,3-b]pyridine, pyrido[2,3-d]pyrimidine, purine, and pteridine and the like. Either or both rings of the bicyclic ring system may be partially saturated, or fully saturated. The bicyclic group may be oxidized on a nitrogen atom to provide the corresponding N-oxide, such as quinoline -N-oxide. The bicyclic group may be oxidized on a sulfur atom to provide the corresponding sulfoxide or sulfone, such as benzothiophene-1-oxide. The bicyclic ring system may contain a carbonyl group on one of the carbon atoms, such as 2-indanone.

Where terms are used in combination, the definition for each individual part of the combination applies unless defined otherwise. For instance, perhaloalkyl refers to an alkyl group, as defined above and perhalo refers to all hydrogen atoms on the alkyl group being substituted with a halogen as define above. An example is trifluoromethyl.

Some of the compounds of the invention have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography. Optically active isomers may be prepared, for example, by resolving racemic derivatives or by asymmetric synthesis. The resolution can be carried out by the methods known to those skilled in the art such as in the presence of a resolving agent, by chromatography, or combinations thereof.

The compounds of Formula (I) may be obtained as inorganic or organic salts using methods known to those skilled in the art (Richard C. Larock, Comprehensive Organic Transformations, VCH publishers, 411–415, 1989). It is well known to one skilled in the art that an appropriate salt form is chosen based on physical and chemical stability, flowability, hydroscopicity and solubility. Pharmaceutically acceptable salts of the compounds of Formula (I) with an acidic moiety may be formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be formed from organic and inorganic acids (i.e. —$N(R_6)_3Q^-$). For example salts may be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids. $Q^-$ is a counterion which includes but is not limited to acetate, chloride, bromide and nitrate. The compounds can also be used in the form of esters, carbamates and other conventional prodrug forms, which when administered in such form, convert to the active moiety in vivo.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

In addition to the utilities, described herein some of the compounds of this invention are intermediates useful for the preparation of other compounds of this invention.

The compounds of this invention may be prepared from: (a) commercially available starting materials (b) known starting materials which may be prepared as described in literature procedures or (c) new intermediates described in the schemes and experimental procedures herein.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps. Appropriate consideration must be made as to the protection of reactive functional groups to prevent undesired side reactions.

Substituents on the starting materials may be incompatible with some of the reaction conditions. Such restrictions to the substituents which are compatible with the reaction conditions will be apparent to one skilled in the art. Reactions were run under inert atmospheres where appropriate.

The preparation of the compounds of this invention encompassed by formulas 2 and 4 is described below in Flowsheet 1 where Z, X, n, $R_3$, $R_4$ $G_1$, $G_2$, $G_3$, and $G_4$ are as described above. Treatment of the unsaturated amide of formula 1 or 2 with an alcohol, amine, mercaptan, or cysteine containing peptide of formula 5 in an inert solvent such as tetrahydrofuran in the presence of a basic catalyst such as triethylamine and the like results in a Michael addition reaction producing the compounds of this invention represented by formulas 2 and 4. In some case where the compounds 1 or 3 already contain a basic functional group, it may not be necessary to add an additional basic catalyst to obtain the compounds of this invention 2 and 4, respectively. In those cases where the product contains more than one asymmetric carbon atom, the resulting diasteromers can be separated by chromatographic methods.

Flowsheet 1

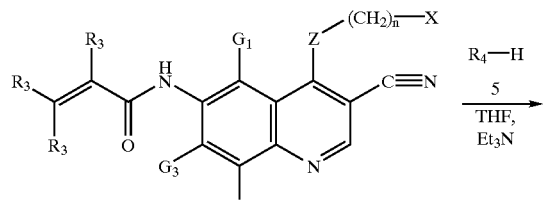

1

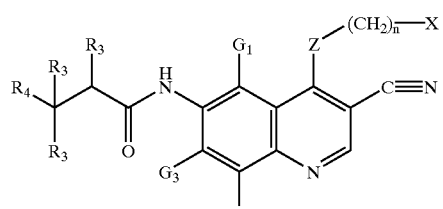

2

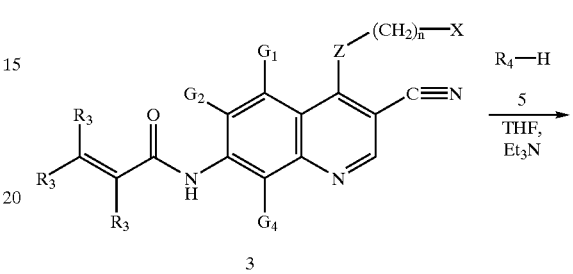

3

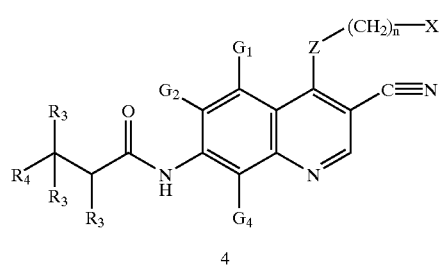

4

Compounds of this invention represented by formulas 8 and 9 may also be prepared as shown below in Flowsheet 2 wherein Z, X, n, $R_3$, $R_4$ $G_1$, $G_2$, $G_3$, and $G_4$ are as described above. J' is the halogen atom Br, I, or Cl and 10 is a primary or secondary amine wherein $R_{10}$ is a radical selected from the group:

$R_8R_9$—CH—N($R_6$)—, $R_7$—(C($R_6$)$_2$)$_p$—N($R_6$)—, Het-(C($R_6$)$_2$)$_q$—N($R_6$)—, ($R_6$)$_2$N—,

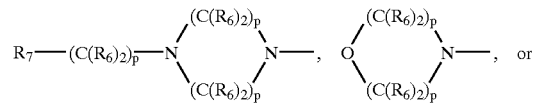, or

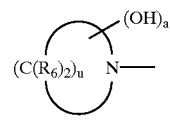

wherein $R_6$, $R_7$, $R_8$, $R_9$, p, u, and q are as defined above. The reaction of compounds 6 or 7 with an amine 10 in an inert solvent such as tetrahydrofuran or acetonitrile results in a two step process involving displacement of the halogen atom with the amine and a Michael addition of the amine to the double bond of the unsaturated amide giving the compounds of this invention 8 or 9, respectively.

Flowsheet 2
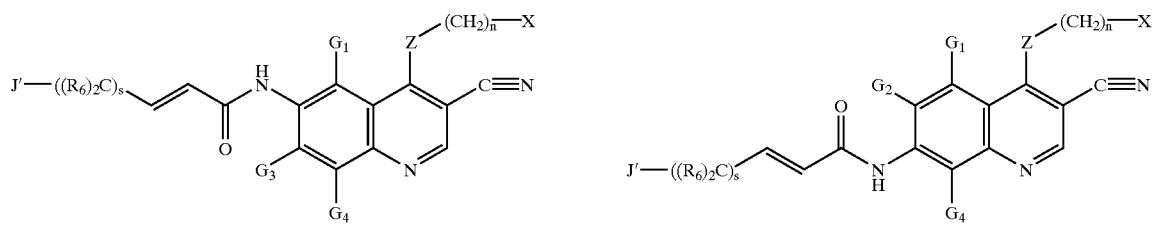
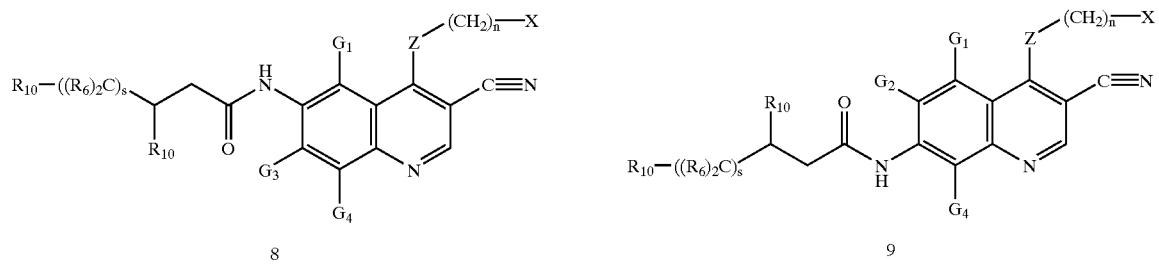
Similar chemistry may be applied to the isomeric intermediates 11–14 to give other compounds of this invention 15–18.
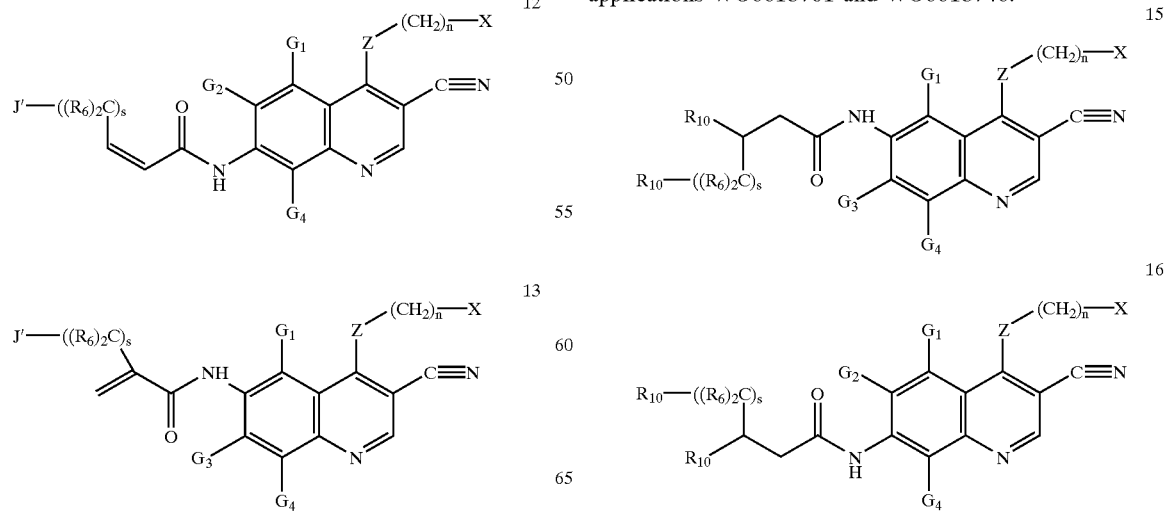
-continued
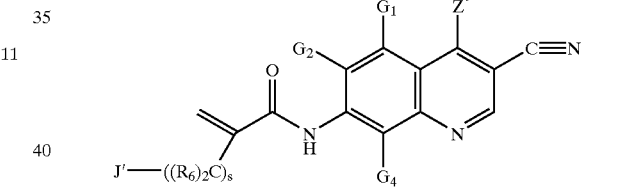
The starting materials 1, 3, 6, 7, and 11–14 needed to prepare the compounds of this invention may be prepared as described in the patent U.S. Pat. No. 6,002,008 and in the applications WO0018761 and WO0018740.

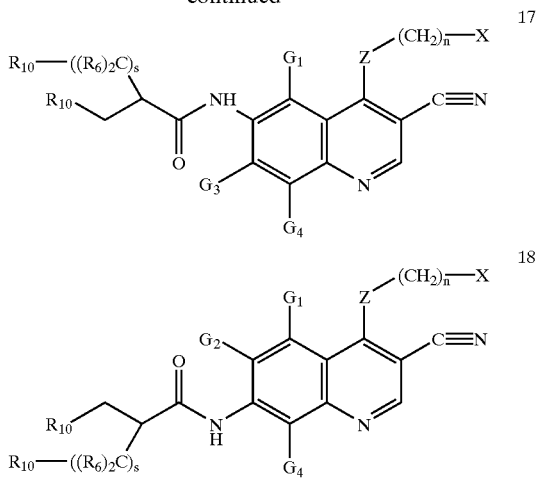

Representative compounds of this invention were evaluated in several standard pharmacological test procedures that showed that the compounds of this invention possess significant activity as inhibitors of protein kinases and are antiproliferative agents. Disease states which can be treated or inhibited by protein kinase inhibitors include those in which the etiology is at least in part caused by a defect upstream in a signaling pathway from a protein kinase (i.e., colon cancer); those in which the etiology is at least in part caused by an overexpressed protein kinase (i.e., lung cancer and colonic polyps); and those in which the etiology is at least in part caused by a dysregulated protein kinase (gene turned on at all times; glioblastoma). Based on the activity shown in the standard pharmacological test procedures, the compounds of this invention are therefore useful as antineoplastic agents. In particular, these compounds are useful in treating, inhibiting the growth of, or eradicating neoplasms such as those of the breast, kidney, bladder, mouth, larynx, esophagus, stomach, colon, ovary, lung, pancreas, liver, prostate and skin.

In addition to having antineoplastic properties, the compounds of the present invention are useful in treating or inhibiting a variety of protein tyrosine kinase-associated disorders including: polycystic kidney disease, colonic polyps, restenosis; atherosclerosis; angiofibromas; hemangiomas; diabetes; acute and chronic nephropathies; Kaposi's sarcoma; neovascularization associated with macular degeneration; rheumatoid arthritis; osteoarthritis; transplant rejection; psoriasis; lupus; graft versus host disease; glomerulonephritis; respiratory and skin allergies; autoimmune alopecia; Autoimmune Hyperthyroidism; multiple sclerosis; atopic dermatitis; and systemic sclerosis; and are useful as antibacterial and antiviral agents.

As used in accordance with this invention, neoplasm and tumor are used interchangeably and mean an abnormal growth of tissue serving no physiological function.

As used in accordance with this invention, the term providing an effective amount of a compound means either directly administering such compound, or administering a prodrug, derivative, or analog which will form an effective amount of the compound within the body.

In addition to the above utilities some of the compounds of this invention are useful for the preparation of other compounds of this invention.

The test procedures used and results obtained are shown below.

STANDARD PHARMACOLOGICAL TEST PROCEDURES

Representative compounds of this invention were evaluated in several standard pharmacological test procedures that showed that the compounds of this invention possess significant activity as inhibitors of protein tyrosine kinases and are antiproliferative agents. Based on the activity shown in the standard pharmacological test procedures, the compounds of this invention are therefore useful as antineoplastic agents. The test procedures used and results obtained are shown below.

INHIBITION OF EPIDERMAL GROWTH FACTOR RECEPTOR KINASE (EGF-R) AND HER2 USING RECOMBINANT ENZYMES

A 1.7 kb cDNA encoding human HER2 cytoplasmic domain (HER2-CD, amino acid 676-1255) and 1.6 kb cDNA for EGFR cytoplasmic domain (EGFR-CD, amino acid 645-1186) were cloned into baculoviral expression vectors, pBlueBacHis2B (Invitrogen) and pFASTBacHTc (GIBCO), separately. A sequence encoding $(His)_6$ is located at the 5' end upstream to HER2 and EGFR sequences. Sf-9 cells were infected at moi=10 for 3 days for protein expression. Sf-9 cell pellets were solubilized on ice in buffer containing 50 mM HEPES, pH 7.4, 10 mM NaCl, 1% Triton, 10 μM ammonium molybdate, 100 μM sodium vanadate, 10 μg/ml aprotinin, 10 μg/ml leupeptin, 10 μg/ml pepstatin, and 16 ug/ml benzamidine HCl for 20 min followed by 20 min centrifugation. Crude extract supernatant was passed through equilibrated Ni-NTA superflow packed column (Qiagen, Valencia, Calif.) and wash with 10 mM, and 100 mM imidazole to remove unspecific binding. Histidine-tagged proteins were eluted with 250 mM and 500 mM imidazole and dialyzed against 50 mM NaCl, 20 mM HEPES, 10% glycerol and 1 μg/ml each of aprotinin, leupeptin and pepstatin for 2 h. All the purification procedure was performed at 4° C. or on ice. Purified materials were subjected for electrophoresis followed by Coommassie blue stain to determine the purity of the preparation and Western blot for the identity of protein. Enzymes were aliquoted and stored at −80° C.

Inhibition of EGFR and HER2 kinase autophosphorylation was measured by a DELFIA/time-resolved fluorometry assay. Compounds were dissolved in 100% DMSO and diluted to the appropriate concentrations with 25 mM HEPES, pH 7.4. In each well, 10 μl of compound was incubated with 10 μl of recombinant EGF-R or HER2 enzyme (1:80 dilution in 100 mM HEPES) for 10 min at room temperature. Then, 10 μl of 5×buffer (containing 20 mM HEPES, 2 mM $MnCl_2$, 100 uM $Na_3VO_4$ and 1 mM DTT) and 20 μl of 0.1 mM ATP/50 mM $MgCl_2$ was added for 1 h. Positive and negative controls were included in each plate by incubation of enzyme with or without ATP/$MgCl_2$. At the end of incubation, liquid was aspirated and washed three times with wash buffer. 75 μl (400 ng).of europium-labeled anti-phosphotyrosine antibody was added to each well for another hour of incubation. After wash, enhancement solution was added and the signal was detected by Victor (Wallac Inc) with excitation at the wavelength of 340 nm and emission at the wavelength of 615 nm. All reagents were supplied by Wallac Inc (Wallac/Perkin-Elimer). Percentage of autophosphorylation inhibition by compound was calculated by 100-[(test-negative control)/(positive control-negative control)]. $IC_{50}$ values were obtained from curves of percentage inhibition with 8 doses of compound. The results of these determinations for the compounds of this invention are shown below in Table 1.

TABLE 1

Inhibition of HER2 and EGF-R Kinases (IC$_{50}$ μg/mL)

| Example | HER2 IC$_{50}$ (μg/mL) | HER2 % Inhibition at 2 μg/mL | EGF-R IC$_{50}$ (μg/mL) |
|---|---|---|---|
| 1 | 0.886 | | |
| 1 | 0.529 | | 3.2 |
| 1 | | 63 | |
| 2 | | 57 | |
| 3 | 4.7 | | 0.33 |
| 5 | 1 | | 1.0 |
| 7 | 0.022 | | |
| 8 | 0.662 | | 1.7 |

INHIBITION OF CANCER CELL GROWTH

Four human carcinoma cell lines, A431 (epidermoid carcinoma), SKBR$_3$ (breast carcinoma), SW620 (colon carcinoma), and MDA-MB435 (breast carcinoma), BT474 (breast carcinoma), and two murine lines, 3T3 (murine fiboblasts) and HER2-3T3 (murine fiboblasts transfected with human HER2) were used for cell proliferation assays. Cells were maintained in RPMI -1640 medium supplemented with 5% fetal bovine serum. Cells were plated in 96-well plates at the densities of 2.5×10$^4$/ml for 3T3 and 3T3/HER2 and 5.0×10$^4$/ml for the rest of the cell lines. On the next day, compounds were dosed at 0.5, 5, 50, 500, and 5000 ng/ml and cultured for 2 days. At the end of incubation, cell survival was determined by the sulforhodamine B assay as previously described (Skehan, P; Stornet, R.; Scudiero, D.; Monks, A.; McMahon, J.; Vistica D., Warren, J.; Bokbosch, H.; Kenny, S.; Boyd, M. New Colorimetric Cytotoxic Assay for Anticancer-Drug Screening. *J. Natl. Cancer Inst.* 1990, 82, 1107–1112). The IC$_{50}$ values (the concentration needed to inhibit cell growth by 50%) were obtained from the growth curves and are shown below in Table 2 where the results of multiple determinations are included.

TABLE 2

Inhibition of Cancer Cell Growth in vitro (IC$_{50}$ μg/mL)

| Example | MDA-MB435 | SW620 | A431 | SKBR3 | 3T3 | HER2-3T3 | BT474 |
|---|---|---|---|---|---|---|---|
| 1 | 0.42 | 0.67 | 0.242 | 0.006 | 0.76 | 0.041 | |
| 1 | 0.6 | 0.34 | 0.37 | 0.009 | 0.7 | 0.04 | 0.02 |
| 1 | 0.09 | >5 | 0.28 | 0.003 | 0.57 | 0.03 | |
| 2 | 3.25 | 2.58 | 0.466 | 0.128 | 4.39 | 0.702 | |
| 2 | 4.05 | 2.95 | 0.572 | 0.129 | 4.47 | 1.26 | |
| 3 | 7.1 | | 0.48 | 0.11 | | | |
| 3 | 2.8 | 1.1 | 0.27 | 0.17 | 1.3 | 1.7 | |
| 5 | 0.36 | | 0.87 | 0.58 | | | |
| 5 | 0.49 | 0.19 | 0.73 | 0.14 | 0.42 | 1.1 | |
| 7 | 0.48 | | 0.13 | 0.0025 | | | |
| 7 | 0.22 | 0.23 | 0.09 | 0.0025 | 0.35 | 0.017 | |
| 7 | | 0.28 | 0.057 | 0.0011 | 0.37 | 0.014 | |
| 8 | >5 | >5 | | 0.098 | >5 | 2.24 | |
| 8 | 3.5 | >5 | 0.2 | 0.107 | >5 | 0.4 | |
| 8 | 1.9 | >5 | 0.21 | 0.208 | >5 | 0.35 | |

IN VIVO INHIBITION OF THE GROWTH OF MURING 3T3 CELLS TRANSFECTED WITH HER2

Representative compounds of this invention (listed below) were evaluated in an in vivo standard pharmacological test procedure which measures their ability to inhibit tumor growth in nude mice. Murine 3T3 fibroblasts, tranfected with Her2 were grown in vitro. Athymic nu/nu female mice (Charles River, Wilmington, Mass.) were used in this in vivo standard pharmacological test procedure. A unit of 2×10$^6$ cells was injected SC into mice (day zero). Beginning on day 1, mice were treated IP every other day for a total of 11 days with a dose of 30 mg/kg/dose of the compound to be evaluated in 0.5% Methocel/0.4% Tween 80. Control animals received vehicle alone. Tumor mass was determined every 7 days [(length×width$^2$)/2] for a period of 21 days. Absolute tumor growth in mgs, (mean tumor mass on days 7, 14 and 21), is calculated for each treatment group. Statistical analysis (Student t-test) of Mean Tumor Mass compares treated verses control groups. A p-value of $\leq 0.05$ indicates a statistically significant reduction in tumor growth of treated group compared to the vehicle control.

The compound of Example 7 was evaluated for its ability to inhibit the growth of a murine fiboblast tumor that was transfected with human HER2 in vivo using the standard pharmacological test procedure described above. The results obtained are shown in Table 3.

TABLE 3

In Vivo Inhibition of the Growth of Tumors Composed of Murine Fiboblasts Transfect with Human HER2 in Mice by the Compound of Example 7.

| a | b | c | d | b | c | d | b | e |
|---|---|---|---|---|---|---|---|---|
| Treatment | Day 7 | % T/C | (p) | Day 14 | % T/C | (p) | Day 21 | S/T |
| Control (0.5% Methocel 0.4% Tween 80) | 260 | | | 2222 | | | | 0/20* |
| Compound of Example 7 | 39 | 15 | <0.01 | 261 | 12 | <0.01 | 1849 | 10/10 |

All compounds administered on days 1, 3, 5, 7, 9 and 11.
b) Mean Tumor Weight in mg.

c) $\% \, T/C = \dfrac{\text{Mean Tumor Weight of Treated Group}}{\text{Mean Tumor Weight of Placebo Group}} \times 100$ d) Statistical analysis (Student's t-test) of Tumor Weight. A p-value of $\leq 0.05$ indicates a statistical significant reduction in Tumor Weight of Treated Group, compared to Placebo Control.
e) S/T = No. Survivors/No, on Day +28 post tumor cell implantation
* Sacrificed on Day 14 due to tumor size.

As shown in Table 3, the compound of Example 7 significantly inhibited tumor growth. At 30 mg/kg (administered i.p.) on day 14, the tumors in the control mice were on average 8.5 times larger than the tumors in the mice that were treated with the compound of Example 7.

Based on the results obtained for representative compounds of this invention, the compounds of this invention are antineoplastic agents which are useful in treating, inhibiting the growth of, or eradicating neoplasms. In particular, the compounds of this invention are useful in treating, inhibiting the growth of, or eradicating neoplasms that express EGFR such as those of the breast, kidney, bladder, mouth, larynx, esophagus, stomach, colon, ovary, or lung. In addition, the compounds of this invention are useful in treating, inhibiting the growth of, or eradicating neoplasms of the breast that express the receptor protein produced by the erbB2 (Her2) oncogene. Based on the results obtained, the compounds of this invention are also useful in the treatment of polycystic kidney disease.

The compounds of this invention may function in vivo as prodrugs. By the result of either a chemical reaction or metabolism, the compounds of this invention can be converted to other compounds that are useful for the treatment of cancer and polycystic kidney disease.

The compounds of this invention may be formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of body weight, optionally given in divided doses two to four times a day, or in sustained release form. The total daily dosage is projected to be from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention can be administered in combination with other antitumor substances or with radiation therapy. These other substances or radiation treatments can be given at the same or at different times as the compounds of this invention. These combined therapies may effect synergy and result in improved efficacy. For example, the compounds of this invention can be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, and antiestrogens such as tamoxifen.

The compounds of this invention and their preparation are illustrated by the following non-limiting examples.

EXAMPLE 1

N-(4-{3-chloro-4-[(4-phenyl-1,3-thiazol-2-yl) sulfanyl]anilino}-3-cyano-7-methoxy-6-quinolinyl)-3,4-bis(dimethylamino)-2-butanamide A 12 ml portion of a 2M solution of dimethylamine in tetrahydrofuran was cooled in an ice bath, and 3.28 g (4.95 mmole) of N-(4-{3-chloro-4-[(4-phenyl-1,3-thiazol-2-yl)sulfanyl]anilino}-3-cyano-7-methoxy-6-quinolinyl)-4-bromo-2-butenamide in 30 ml of N,N-dimethylformamide was added dropwise. The reaction warmed to come to room temperature, and stirred for a total of about 24 hours. The reaction was poured onto ice, and the resulting mixture was extracted with 1:1 (v/v) ethyl acetate-tetrahydrofuran. The solvents were removed in vacuo, and the residue was chromatographed on silica gel. The column was washed with 1:19 (v/v) methanol-ethyl acetate, then the product was eluted with 94:5:1 (v/v/v) ethyl acetate-methanol-triethylamine as a mixture of the title compound and N-(4-{3-chloro-4-[(4-phenyl-1,3-thiazol-2-yl)sulfanyl]anilino}-3-cyano-7-methoxy-6-quinolinyl)-4-(dimethylamino)-2-butenamide. This mixture was re-chromatographed on silica gel, and the title compound was eluted with 99:1 (v/v) methylene chloride-triethylamine. This gave 724 mg (23%) of N-(4-{3-chloro-4-[(4-phenyl-1,3-thiazol-2-yl)sulfanyl]anilino}-3-cyano-7-methoxy-6-quinolinyl)-3,4-bis(dimethylamino)-2-butanamide. Electrospray MS (M+H)= 672.2, (M+2H)=336.8.

EXAMPLE 2

N-[4-(3-Chloro-4-fluoro-phenylamino)-3-cyano-7-methoxy-quinolin-6-yl]-3,4-bis-(3-hydroxy-pyrrolidin-1-yl)-butyramide N-[4-(3-Chloro-4-fluoro-phenylamino)-3-cyano-7-ethoxy-6-quinolinyl)-4-bromo-2-butenamide (150 mg, 0.3 mmol) in 0.7 mL of DMF was reacted with (R)-(+)-3- pyrrolidinol (0.2 mL, 2.4 mmol) at room temperature. After reacting for 4 hours, the reaction solution was added into saturated sodium bicarbonate solution. The resulting precipitate was filtered and washed with water and ether consecutively to give 150 mg of the title compound as a light brown solid, mp 139–143° C.; MS (ES) m/z calcd. 583.2236, found 583.2242 (M+1).

EXAMPLE 3

N-[4-(3-Chloro-4-fluoroanilino)-3-cyano-7-ethoxy-6-quinolinyl]-3-(dimethylamino)butanamide To a stirred solution of N-[4-(3-chloro-4-fluoroanilino)-3-cyano-7-ethoxy-6-quinolinyl]-2-butenamide (0.212 g, 0.50 mmol) in 25 ml of 2.0 M dimethylamine in tetrahydrofuran was added 0.02 ml of 40% aqueous Triton B. After 66 h at 25° C. the solution was concentrated, and the residue was partitioned between methylene chloride and water. The residue from the organic layer was dissolved in ether, and the solution was passed onto a pad of hydrous magnesium silicate. The pad was washed with ether and ethyl acetate to give the product as an amber foam after evaporation (0.23 g). Mass spectrum (electrospray, m/e) 469.9 (M+H)$^+$, 235.5 (M+2H)$^{+2}$.

EXAMPLE 4

N-{4-[4-(Benzyloxy)-3-chloroanilino]-3-cyano-7-ethoxy-6-quinolinyl}6-chloro-2-hexenamide To a stirred solution of 6-amino-4-[4-(benzyloxy)-3-chloroanilino]-7-ethoxy-3-quinolinecarbonitrile (0.89 g, 2.0 mmol) and diisopropylethylamine (0.47 ml, 2.7 mmol) in 16 ml of tetrahydrofuran at 0° C. was added a freshly-prepared solution of 6-chloro-2-hexenoyl chloride in 4 ml of tetrahydrofuran during 30 s. The mixture was then stirred at 25° C. for 2.5 h and partitioned between ethyl acetate and water. The organic layer was washed with water, dried and concentrated. The residue was chromatographed on silica gel with methylene chloride-ethyl acetate to give 0.83 g of amber solid; mass spectrum (electrospray, m/e) 574.8 (M+H)$^+$.

EXAMPLE 5

N-{4-[4-(Benzyloxy)-3-chloroanilino]-3-cyano-7-ethoxy-6-quinolinyl}-3,6-bis(dimethylamino)hexanamide A stirred mixture of N-{4-[4-(Benzyloxy)-3-chloroanilino]-3-cyano-7-ethoxy-6-quinolinyl}6-chloro-2-hexenamide (0.58 g, 1.0 mmol), NaI (0.15 g, 1.0 mmol), tetrabutylammonium iodide (74 mg, 0.20 mmol), 4.0 ml of dimethylformamide, and 10 ml of 2.0 M dimethylamine in tetrahydrofuran was heated at 50° C. for 8 h. After the addition of 5 ml more 2.0 M dimethylamine in tetrahydrofuran the mixture was heated at 50° C. for an additional 8 h. After evaporation of the dimethylamine and tetrahydrofuran, the mixture was stirred in water, brought to pH~9 with potassium carbonate, and filtered. The crude product was washed with water, dried, and chromatographed on silica gel with methylene chloride-ethyl acetate-methanol-triethylamine to give 464 mg of the title compound as an off-white solid; mass spectrum (electrospray, m/e) 628.9 (M+H)$^+$, 315.1 (M+2H)$^{+2}$.

EXAMPLE 6

(E)-N-{4-[4-(Benzyloxy)-3-chloroanilino]-3-cyano-7-ethoxy-6-quinolinyl}-4-chloro-2-butenamide and (E)-N-{4-[4-(Benzyloxy)-3-chloroanilino]-3-cyano-7-ethoxy-6-quinolinyl}-4-bromo-2-butenamide A mixture of 3.4 g (7.66 mmol) of 6-amino-4-[4-(benzyloxy)-3-chloroanilino]-7-ethoxy-3-quinolinecarbonitrile and N,N-diisopropylethylamine (2.65 mL, 15.3 mmol), were stirred in 68 mL of tetrahydrofuran, and cooled to 0° C. To this 4-bromo-but-2-enoylchloride (1.13 mL, 9.95 mmol) was added dropwise over a period of one hour. After stirring for 30 minutes, the solvent was evaporated, and the resulting oil was stirred with saturated sodium bicarbonate, and extracted with ethyl acetate. The layers were separated, and the organic layer was dried over sodium sulfate and evaporated to an oil. Purification was carried out by flash chromatography (50% ethyl acetate in methylene chloride), to give a tan solid (7.3 g, 80% yield), consisting of 50% of (E)-N-{4-[4-(benzyloxy)-3-chloroanilino]-3-cyano-7-ethoxy-6-quinolinyl}-4-chloro-2-butenamide and 50% of (E)-N-{4-[4-(benzyloxy)-3-chloroanilino]-3-cyano-7-ethoxy-6-quinolinyl}-4-bromo-2-butenamide, mp 117–120° C.;

MS (ESI) 547.1 (M+1), 593.0 (M+1).

Analysis for (50% $C_{29}H_{24}BrClN_4O_3$+50% $C_{29}H_{24}Cl_2N_4O_3$).0.8H$_2$O:

Found: C, 59.32; H, 4.07; N, 9.45.

Calcd: C, 59.64; H, 4.42; N, 9.59.

EXAMPLE 7

N-{4-[4-(Benzyloxy)-3-chloroanilino]-3-cyano-7-ethoxy-6-quinolinyl}-3,4-di(1-pyrrolidinyl)butanamide An amount of 612 mg (1.1 mmol) of (E)-N-{4-[4-(benzyloxy)-3-chloroanilino]-3-cyano-7-ethoxy-6-quinolinyl}-4-chloro-2-butenamide, and (E)-N-{4-[4-(benzyloxy)-3-chloroanilino]-3-cyano-7-ethoxy-6-quinolinyl}-4-bromo-2-butenamide, were stirred in 6 mL of N,N-dimethylformamide and cooled to −50° C. Pyrrolidine (55 μL, 0.66 mmol), was added dropwise over a period of 30 min. After stirring for 2 hrs at −50° C., another 0.250 mL (3.0 mmol) of pyrrolidine was added dropwise over a period of 1.5 hrs, and the reaction mixture was warmed to room temperature for 16 hrs. A solution of saturated sodium bicarbonate was added, and the product was extracted with ethyl acetate and methylene chloride. Both organic layers were combined, dried over sodium sulfate, poured over a hydrous magnesium silicate plug, and evaporated to an oil. Purification was carried out by flash chromatography (40:4:2=ethyl acetate: methanol:ammonium hydroxide), and preparative thin layer chromatography (40:4:1=ethyl acetate:methanol:triethylamine), to give the title compound as an orange solid (284 mg, 40%), mp 85–87° C.; $^1$H NMR (DMSO-d$_6$) δ10.59 (bs, 1H), 9.57 (s, 1H), 9.01 (s, 1H), 8.46 (s, 1H), 7.51–7.33 (m, 7H), 7.26–7.16 (m, 2H), 5.21 (s, 2H), 4.23 (q, 2H), 2.98 (bs, 1H), 2.71–2.60 (m, 8H), 2.49 (m, 2H) 1.74 (m, 5H), 1.64 (m, 5H), 1.43 (t, 3H); HRMS (ESI-FTMS) 653.29959 (M+1).

EXAMPLE 8

(2R)-2-amino-5-({2-[(carboxymethyl)amino]-1-[({3-{[4-(3-chloro-4-fluoroanilino)-3-cyano-7-ethoxy-6-quinolinyl]amino}-1-[(dimethylamino)methyl]-3-oxopropyl}sulfanyl)methyl]-2-oxoethyl}amino)-5-oxopentanoic acid A mixture of 0.50 g (1.07 mmol) of 4-dimethylamino-but-2-enoic acid [4-(3-chloro-4-fluoro-phenylamino)-3-cyano-7-ethoxy-quinolin-6-yl]-amide, 0.328 g (1.07 mmol) of glutathione, and 0.2 mL of triethylamine in a solvent mixture consisting of 10 mL of methanol, 4 mL of water, and 4 mL of tetrahydrofuran was stirred for 7 h and then stored overnight in the refrigerator. The solvents were remove at reduced pressure at 30° C. Ethanol was added and removed three times giving 0.81 g of the title compound as a tan powder. A sample of this was purified by HPLC. The product was then isolated as the trifluoroacetate salt. Analysis for $C_{34}H_{40}N_8O_8ClFS+(C_2HF_3O_2)_3$; calcd: C, 43.00, H, 3.88, N, 10.03, Cl, 3.17; found: C, 42.23, H, 4.17, N, 10.03, Cl, 3.23.

EXAMPLE 9

N-{4-[4-(Benzyloxy)-3-chloroanilino]-3-cyano-7-ethoxy-6-quinolinyl}-3,4-bis(dimethylamino)butanamide A solution of (E)-N-{4-[4-(benzyloxy)-3-chloroanilino]-3-cyano-7-ethoxy-6-quinolinyl}-4-(dimethylamino)-2-butenamide (400 mg, 0.719 mmol) and 1.5 mL of 2N dimethylamine in THF was heated at 36° C. in a sealed tube for 20 hours. After the volatile solvents were stripped off, the residue was treated with 1.5 mL of 2N dimethylamine in THF, and heated again at 36° C. in a sealed tube for 20 hours. After the solvent was removed, the residue was purified by preparatory TLC (developed in ethyl acetate:methanol:triethylamine=10:1:1) to yield 260 mg of the title compound as a yellow solid (yield: 60%), mp 102–104° C.; MS (ES) 601.3 (M+1).

EXAMPLE 10

N-{4-[4-(Benzyloxy)-3-chloroanilino]-3-cyano-7ethoxy-6-quinolinyl}-3,4-bis(dimethylamino)butanamide A solution of N-{4-[4-(Benzyloxy)-3-chloroanilino]-3-cyano-7ethoxy-6-quinolinyl}-3,4-bis(dimethylamino)butanamide (400 mg, 0.719 mmol) and 1.5 mL of 2N dimethylamine in THF was heated at 36° C. in a sealed tube for 20 hours. After the volatile solvents were stripped off, the residue was treated with 1.5 mL of 2N dimethylamine in THF, and heated again at 36° C. in a sealed tube for 20 hours. After the solvent was removed, the residue was purified by preparatory TLC (developed in ethyl acetate:methanol:triethylamine=10:1:1) to yield 260 mg of a yellow solid (yield: 60%), mp 102–104° C.; MS (ES) 601.3 (M+1).

What is claimed is:

1. A compound of Formula (I) represented by the structure:

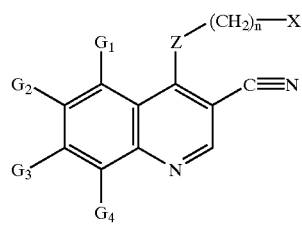

wherein:

Z is —NH—,

X is a phenyl which may optionally be mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or X is the radical

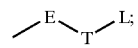

E is a phenyl optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

T is substituted on E at carbon and is

—NH(CH$_2$)$_m$—, —O(CH$_2$)$_m$—, —S(CH$_2$)$_m$—, —NR(CH$_2$)$_m$—, —(CH$_2$)$_m$— —(CH$_2$)$_m$NH—, —(CH$_2$)$_m$O—, —(CH$_2$)$_m$S—, or —(CH$_2$)$_m$NR—;

L is an aryl ring optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy ($C_6H_5$S—), benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

Pyridinyl, pyrimidinyl, or aryl are pyridinyl, pyrimidinyl, or aryl radicals, respectively, optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

$G_3$ is alkoxy of 1 to 6 carbon atoms;

$G_2$ is $R_2$NH;

$G_1$ and $G_4$ are each, independently, hydrogen, halogen, alkyl of 1 to 6 carbon atoms, alkenyl of 2 to 6 carbon atoms, alkynyl of 2 to 6 carbon atoms, alkenyloxy of 2 to 6 carbon atoms, alkynyloxy of 2 to 6 carbon atoms, hydroxymethyl, halomethyl, alkanoyloxy of 2 to 6 carbon atoms, alkenoyloxy of 3 to 8 carbon atoms, alkynoyloxy of 3 to 8 carbon atoms, alkanoyloxymethyl of 2 to 7 carbon atoms, alkenoyloxymethyl of 4 to 9 carbon atoms, alkynoyloxymethyl of 4 to 9 carbon atoms, alkoxymethyl of 2 to 7 carbon atoms, alkoxy of 1 to 6 carbon atoms, alkylthio of 1 to 6 carbon atoms (alkyl$C_1$–$C_6$)S—, alkylsulphinyl of 1 to 6 carbon atoms, alkylsulphonyl of 1 to 6 carbon atoms, alkylsulfonamido of 1 to 6 carbon atoms, alkenylsulfonamido of 2 to 6 carbon atoms, alkynylsulfonamido of 2 to 6 carbon atoms, hydroxy, trifluoromethyl, trifluoromethoxy, cyano, nitro, carboxy, carboalkoxy of 2 to 7 carbon atoms, carboalkyl of 2 to 7 carbon atoms, phenoxy, phenyl, thiophenoxy ($C_6$—$H_5$S—), benzyl, amino, hydroxyamino, alkoxyamino of 1 to 4 carbon atoms, alkylamino of 1 to 6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6 to 12 carbon atoms, phenylamino, benzylamino, $R_2$NH,

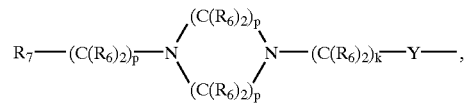

$R_8R_9$—CH—M—$(C(R_6)_2)_k$—Y—

$R_7$—$(C(R_6)_2)_g$—Y—, $R_7$—$(C(R_6)_2)_p$—M—$(C(R_6)_2)_k$—Y—, or Het-$(C(R_6)_2)_q$—W—$(C(R_6)_2)_k$—Y—,

Y is a divalent radical selected from the group consisting of

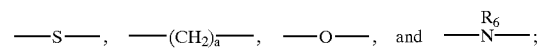

$R_7$ is —$NR_6R_6$—$OR_6$, —J, —$N(R_6)_3{}^+Q^-$, or —$NR_6(OR_6)$;

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is a —heterocyclic radical selected from the group consisting of pyrrolidine, aziridine, imidazole, 1,2,3-triazole, 1,2,4-triazole, thiazole, thiazolidine, tetrazole, furan, thiophene, tetrahydrothiophene, tetrahydrofuran, and;

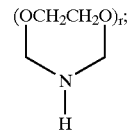

which may be optionally mono- or di-substituted on carbon with $R_6$, hydroxy, —$N(R_6)_2$, —$OR_6$, —$(C(R_6)_2)_s OR_6$ or —$(C(R_6)_2)_s N(R_6)_2$;

optionally mono-substituted on nitrogen with $R_6$; and optionally mono or di-substituted on a saturated carbon with divalent radicals —O— or —$O(C(R_6)_2)_s O$—;

$R_6$ is hydrogen, alkyl of 1 to 6 carbon atoms, alkenyl of 2 to 6 carbon atoms, alkynyl of 2 to 6 carbon atoms, cycloalkyl of 3 to 7 carbon atoms, carboalkyl of 2 to 7 carbon atoms, carboxyalkyl 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms (alkyl$C_1$–$C_6$)S—, hydroxy, carboxyl, carboalkoxy of 2 to 7 carbon atoms, phenoxy, phenyl, thiophenoxy ($C_6H_5$S—), benzoyl, benzyl, phenylamino, benzylamino, alkanoylamino of 1 to 6 carbon atoms, or alkyl of 1 to 6 carbon atoms; provided that the alkenyl or alkynyl moiety is bound to a nitrogen or oxygen atom through a saturated carbon atom;

$R_2$, is selected from the group consisting of

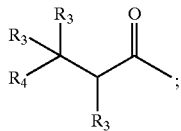

$R_3$ is hydrogen, alkyl of 1 to 6 carbon atoms, carboxy, carboalkoxy of 1 to 6 carbon atoms, phenyl, carboalkyl of 2 to 7 carbon atoms,

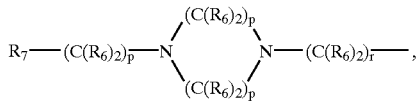

$R_7$—$(C(R_6)_2)_s$—, $R_7$—$(C(R_6)_2)_p$—M—$C(R_6)_2)_r$—,
$R_8R_9$—CH—M—$(C(R_6)_2)_r$—, or Het-$(C(R_6)_2)_q$—W—$(C(R_6)_2)_r$—;
$R_4$ is —$NR_6R_6$, —$OR_6$, —$SR_6$,
$R_7$—$(C(R_6)_2)_p$—S—, $R_7$—$(C(R_6)_2)_p$—N($R_6$)—, $R_7$—$(C(R_6)_2)_p$—O—,
$R_8R_9$—CH—N($R_6$)—, $R_8R_9$—CH—S—, $R_8R_9$—CH—O—,
Het-$(C(R_6)_2)_q$—N($R_6$)—, Het-$(C(R_6)_2)_q$—S—, Het-$(C(R_6)_2)_q$—O—,

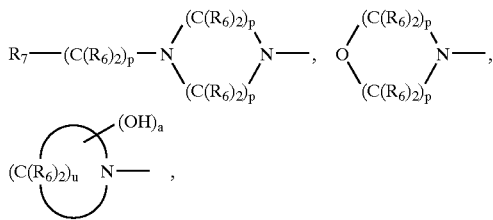

cysteine, or a peptide comprised of 2 to 10 native amino acid residues containing at least one unoxidized cysteine residue wherein $R_4$ is bound to the rest of the molecule through the sulfur atom of one or more of the cysteine residues;

$R_8$ and $R_9$ are each, independently, —$(C(R_6)_2)_r NR_6R_6$, or —$(C(R_6)2)_r$ $OR_6$;

J is independently hydrogen, chlorine, fluorine, or bromine;

a is an integer of 0–1;
g is an integer of 1–6;
k is an integer of 0–4;
n is an integer of 0–1;
m is an integer of 0–3;
p is an integer of 2–4;
q is an integer of 0–4;
r is an integer of 1–4;
s is an integer of 1–6
u is an integer of 2–6;

$Q^-$ is a counterion selected from salts formed from organic and inorganic acids;

provided that:
a. when $R_6$ is alkenyl of 2 to 7 carbon atoms or alkynyl of 2 to 7 carbon atoms, such alkenyl or alkynyl moiety is bound to a nitrogen or oxygen atom through a saturated carbon atom;

b. when Y is —$NR_6$— and $R_7$ is —$NR_6R_6$, —$N(R_6)_3$ $^+Q^-$, or —$NR_6(OR_6)$, then g is an integer of 2 to 6;
c. when M is —O— and $R_7$ is —$OR_6$ then p is an integer of 1 to 4;
d. when Y is —$NR_6$— then k is an integer of 2 to 4;
e. when Y is —O— and M or W is —O— then k is an integer of 1 to 4;
f. when W is not a bond with Het bonded through a nitrogen atom then q is an integer of 2 to 4 and when W is a bond with Het bonded through a nitrogen atom and Y is —O— or —$NR_6$— then k is an integer of 2 to 4;

or a pharmaceutically acceptable salt thereof.

2. The compound according to claim 1 wherein Z is —NH—, n is an integer of 0, X is phenyl optionally substituted and $G_1$ and $G_4$ are H or a pharmaceutically acceptable salt thereof.

3. The compound according to claim 1 herein X is the radical:

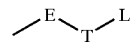

and E is phenyl optionally substituted, or a pharmaceutically acceptable salt thereof.

4. The compound according to claim 3 wherein L is 5 or 6-membered heteroaryl ring or a pharmaceutically acceptable salt thereof.

5. The compound according to claim 4 wherein the heteroaryl ring is selected from the group consisting of pyridine, pyrimidine, imidazole, thiazole, thiazolidine, pyrrole, furan, thiophene, oxazole, and 1,2,4-triazole or a pharmaceutically acceptable salt thereof.

6. The compound according to claim 3 wherein L is an optionally substituted aryl ring or a pharmaceutically acceptable salt thereof.

7. The compound according to claim 1, which is:
N-(4-{3-chloro-4-[(4-phenyl-1,3-thiazol-2-yl)sulfanyl]anilino}-3-cyano-7-methoxy-6-quinolinyl)-3,4-bis(dimethylamino)-2-butanamide or a pharmaceutically acceptable salt thereof.

8. The compound according to claim 1, which is:
N-[4-(3-chloro-4-fluoro-phenylamino)-3-cyano-7-methoxy-quinolin-6-yl]-3,4-bis-(3-hydroxy-pyrrolidin-1-yl)-butyramide or a pharmaceutically acceptable salt thereof.

9. The compound according to claim 1, which is:
N-[4-(3-chloro-4-fluoroanilino)-3-cyano-7-ethoxy-6-quinolinyl]-3-(dimethylamino)butanamide or a pharmaceutically acceptable salt thereof.

10. The compound according to claim 1, which is:
N-{4-[4-(benzyloxy)-3-chloroanilino]-3-cyano-7-ethoxy-6-quinolinyl}-3,6-bis(dimethylamino)hexanamide or a pharmaceutically acceptable salt thereof.

11. The compound according to claim 1, which is:
N-{4-[4-(benzyloxy)-3-chloroanilino]-3-cyano-7-ethoxy-6-quinolinyl}-3,4-di(1-pyrrolidinyl)butanamide or a pharmaceutically acceptable salt thereof.

12. The compound according to claim 1, which is:
(2R)-2-amino-5-({2-[(carboxymethyl)amino]-1-[({3-{[4-(3-chloro-4-fluoroanilino)-3-cyano-7-ethoxy-6-quinolinyl]amino}-1-[(dimethylamino)methyl]-3-oxopropyl}sulfanyl)methyl]-2-oxoethyl}amino)-5-oxopentanoic acid or a pharmaceutically acceptable salt thereof.

13. The compound according to claim 1, which is:
N-{4-[4-(benzyloxy)-3-chloroanilino]-3-cyano-7-ethoxy-6-quinolinyl}-3,4-bis(dimethylamino)butanamide or a pharmaceutically acceptable salt thereof.

14. A method of treating the growth of neoplasms in a mammal in need thereof which comprises administering to said mammal an effective amount of a compound of Formula (I) represented by the structure

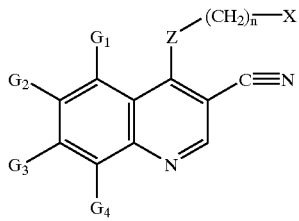

wherein:
Z is —NH—;
X is a phenyl which may optionally be mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or
X is the radical

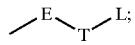

E is a phenyl optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

T is substituted on E at carbon and is
—NH($CH_2$)$_m$—, —O($CH_2$)$_m$—, —S($CH_2$)$_m$—, —NR($CH_2$)$_m$—, —($CH_2$)$_m$—
—($CH_2$)$_m$NH—, —($CH_2$)$_m$O—, —($CH_2$)$_m$S—, or —($CH_2$)$_m$NR—;

L is an aryl ring optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy ($C_6H_5$S—), benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

Pyridinyl, pyrimidinyl, or aryl are pyridinyl, pyrimidinyl, or aryl radicals, respectively, optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

$G_3$ is alkoxy of 1 to 6 carbon atoms;

G2 is $R_2NH—$;

$G_1$, $G_3$ and $G_4$ are each, independently, hydrogen, halogen, alkyl of 1 to 6 carbon atoms, alkenyl of 2 to 6 carbon atoms, alkynyl of 2 to 6 carbon atoms, alkenyloxy of 2 to 6 carbon atoms, alkynyloxy of 2 to 6 carbon atoms, hydroxymethyl, halomethyl, alkanoyloxy of 2 to 6 carbon atoms, alkenoyloxy of 3 to 8 carbon atoms, alkynoyloxy of 3 to 8 carbon atoms, alkanoyloxymethyl of 2 to 7 carbon atoms, alkenoyloxymethyl of 4 to 9 carbon atoms, alkynoyloxymethyl of 4 to 9 carbon atoms, alkoxymethyl of 2 to 7 carbon atoms, alkoxy of 1 to 6 carbon atoms, alkylthio of 1 to 6 carbon atoms (alkyl$C_1$–$C_6$)S—, alkylsulphinyl of 1 to 6 carbon atoms, alkylsulphonyl of 1 to 6 carbon atoms, alkylsulfonamido of 1 to 6 carbon atoms, alkenylsulfonamido of 2 to 6 carbon atoms, alkynylsulfonamido of 2 to 6 carbon atoms, hydroxy, trifluoromethyl, trifluoromethoxy, cyano, nitro, carboxy, carboalkoxy of 2 to 7 carbon atoms, carboalkyl of 2 to 7 carbon atoms, phenoxy, phenyl, thiophenoxy ($C_6H_5S—$), benzyl, amino, hydroxyamino, alkoxyamino of 1 to 4 carbon atoms, alkylamino of 1 to 6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6 to 12 carbon atoms, phenylamino, benzylamino, $R_2NH$,

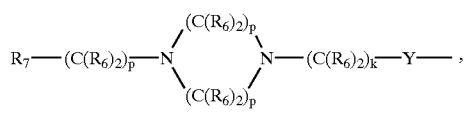

$R_8R_9$—CH—M—$(C(R_6)_2)_k$—Y—
$R_7$—$(C(R_6)_2)_g$—Y—, $R_7$—$(C(R_6)_2)_p$—M—$(C(R_6)_2)_k$—Y—, or Het-$(C(R_6)_2)_q$—W—$(C(R_6)_2)_k$—Y—,

Y is a divalent radical selected from the group consisting of

—S—, —$(CH_2)_a$—, —O—, and
—$\underset{R_6}{N}$—;

$R_7$ is —$NR_6R_6$, —$OR_6$, —J, —$N(R_6)_3$ $^+Q^-$ or —$NR_6$($OR_6$);

M is >$NR_6$, —O—, >N—$(C(R_6)_2)_p NR_6R_6$, or >N—$(C(R_6)_2)_p$—$OR_6$;

W is >$NR_6$, —O— or is a bond;

Het is a heterocyclic radical selected from the group consisting of pyrrolidine, aziridine, imidazole, 1,2,3-triazole, 1,2,4-triazole, thiazole, thiazolidine, tetrazole, furan, thiophene, tetrahydrothiophene, tetrahydrofuran, and

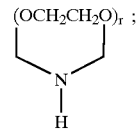

which may be optionally mono- or di-substituted on carbon with $R_6$, hydroxy, —$N(R_6)_2$, —$OR_6$, —$(C(R_6)_2)_s OR_6$ or —$(C(R_6)_2)_s N(R_6)_2$;

optionally mono-substituted on nitrogen with $R_6$; and optionally mono or di-substituted on a saturated carbon with divalent radicals —O— or —$O(C(R_6)_2)_s O—$;

$R_6$ is hydrogen, alkyl of 1 to 6 carbon atoms, alkenyl of 2 to 6 carbon atoms, alkynyl of 2 to 6 carbon atoms, cycloalkyl of 3 to 7 carbon atoms, carboalkyl of 2 to 7 carbon atoms, carboxyalkyl 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms (alkyl$C_1$–$C_6$)S—, hydroxy, carboxyl, carboalkoxy of 2 to 7 carbon atoms, phenoxy, phenyl, thiophenoxy ($C_6H_5S—$), benzoyl, benzyl, phenylamino, benzylamino, alkanoylamino of 1 to 6 carbon atoms, or alkyl of 1 to 6 carbon atoms; provided that the alkenyl or alkynyl moiety is bound to a nitrogen or oxygen atom through a saturated carbon atom;

$R_2$, is selected from the group consisting of

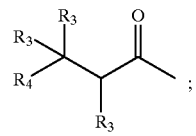

$R_3$ is hydrogen, alkyl of 1 to 6 carbon atoms, carboxy, carboalkoxy of 1 to 6 carbon atoms, phenyl, carboalkyl of 2 to 7 carbon atoms,

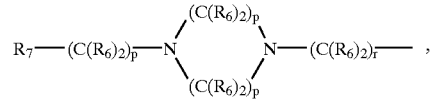

$R_7$—$(C(R_6)_2)_s$—, $R_7$—$(C(R_6)_2)_p$—M—$C(R_6)_2)_r$—, $R_8R_9$—CH—M—$(C(R_6)_2)_r$—, or Het-$(C(R_6)_2)_q$—W—$(C(R_6)_2)_r$—;

$R_4$ is —$NR_6R_6$, —$OR_6$, —$SR_6$, $R_7$—$(C(R_6)_2)_p$—S—, $R_7$—$(C(R_6)_2)_p$—$N(R_6)$—, $R_7$—$(C(R_6)_2)_p$—O—, $R_8R_9$—CH—$N(R_6)$—, $R_8R_9$—CH—S—, $R_8R_9$—CH—O—,

Het-$(C(R_6)_2)_q$—$N(R_6)$—, Het-$(C(R_6)_2)_q$—S—, Het-$(C(R_6)_2)_q$—O—,

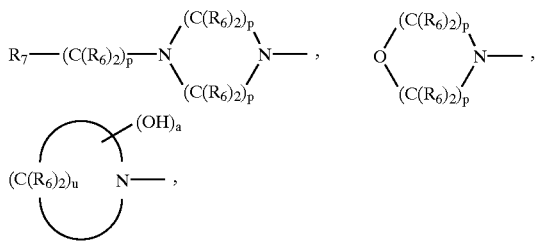
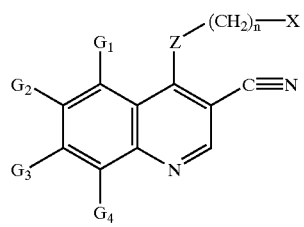

cysteine, or a peptide comprised of 2 to 10 native amino acid residues containing at least one unoxidized cysteine residue wherein $R_4$ is bound to the rest of the molecule through the sulfur atom of one or more of the cysteine residues;

$R_8$ and $R_9$ are each, independently, $-(C(R_6)_2)_rNR_6R_6$, or $-(C(R_6)2)_rOR_6$;

J is independently hydrogen, chlorine, fluorine, or bromine;

a is an integer of 0–1;

g is an integer of 1–6;

k is an integer of 0–4;

n is an integer of 0–1;

m is an integer of 0–3;

p is an integer of 2–4;

q is an integer of 0–4;

r is an integer of 1–4;

s is an integer of 1–6 u is an integer of 2–6;

$Q^-$ is a counterion selected from salts formed from organic and inorganic acids;

provided that:
  a. when $R_6$ is alkenyl of 2 to 7 carbon atoms or alkynyl of 2 to 7 carbon atoms, such alkenyl or alkynyl moiety is bound to a nitrogen or oxygen atom through a saturated carbon atom;
  b. when Y is $-NR_6-$ and $R_7$ is $-NR_6R_6$, $-N(R_6)_3$ $^+Q^-$, or $-NR_6(OR_6)$, then g is an integer of 2 to 6;
  c. when M is $-O-$ and $R_7$ is $-OR_6$ then p is an integer of 1 to 4;
  d. when Y is $-NR_6-$ then k is an integer of 2 to 4;
  e. when Y is $-O-$ and M or W is $-O-$ then k is an integer of 1 to 4;
  f. when W is not a bond with Het bonded through a nitrogen atom then q is an integer of 2 to 4 and when W is a bond with Het bonded through a nitrogen atom and Y is $-O-$ or $-NR_6-$ then k is an integer of 2 to 4;

or a pharmaceutically acceptable salt thereof.

15. The method according to claim 14 wherein the neoplasm is selected from the group consisting of breast, kidney, bladder, mouth, larynx, esophagus, stomach, colon, ovary, and lung.

16. A method of treating the progression of polycystic kidney disease in a mammal in need thereof which comprises administering to said mammal an effective amount of a compound of Formula (I) represented by the structure:

wherein:
  Z is $-NH-$; or
  X is a phenyl which may optionally be mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or X is the radical

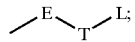

E is a phenyl optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$) S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

T is substituted on E at carbon and is
$-NH(OH_2)_m-$, $-O(CH_2)_m-$, $-S(CH_2)_m-$, $-NR(CH_2)_m-$, $-(CH_2)_m-$
$-(CH_2)_mNH-$, $-(CH_2)_mO-$, $-(CH_2)_mS-$, or $-(CH_2)_mNR-$;

L is an aryl ring optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy ($C_6H_5$S—), benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

Pyridinyl, pyrimidinyl, or aryl are pyridinyl, pyrimidinyl, or aryl radicals, respectively, optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto,), and benzylamino;

$G_3$ is an alkoxy of 1 to 6 carbon atoms;

$G_2$ is $R_2$NH;

$G_1$, and $G_4$ are each, independently, hydrogen, halogen, alkyl of 1 to 6 carbon atoms, alkenyl of 2 to 6 carbon atoms, alkynyl of 2 to 6 carbon atoms, alkenyloxy of 2 to 6 carbon atoms, alkynyloxy of 2 to 6 carbon atoms, hydroxymethyl, halomethyl, alkanoyloxy of 2 to 6 carbon atoms, alkenoyloxy of 3 to 8 carbon atoms, alkynoyloxy of 3 to 8 carbon atoms, alkanoyloxymethyl of 2 to 7 carbon atoms, alkenoyloxymethyl of 4 to 9 carbon atoms, alkynoyloxymethyl of 4 to 9 carbon atoms, alkoxymethyl of 2 to 7 carbon atoms, alkoxy of 1 to 6 carbon atoms, alkylthio of 1 to 6 carbon atoms (alkyl$C_1$–$C_6$)S—, alkylsulphinyl of 1 to 6 carbon atoms, alkylsulphonyl of 1 to 6 carbon atoms, alkylsulfonamido of 1 to 6 carbon atoms, alkenylsulfonamido of 2 to 6 carbon atoms, alkynylsulfonamido of 2 to 6 carbon atoms, hydroxy, trifluoromethyl, trifluoromethoxy, cyano, nitro, carboxy, carboalkoxy of 2 to 7 carbon atoms, carboalkyl of 2 to 7 carbon atoms, phenoxy, phenyl, thiophenoxy ($C_6H_5$S—), benzyl, amino, hydroxyamino, alkoxyamino of 1 to 4 carbon atoms, alkylamino of 1 to 6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6 to 12 carbon atoms, phenylamino, benzylamino, $R_2$NH,

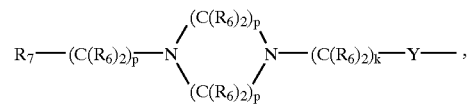

$R_8R_9$—CH—M—(C($R_6$)$_2$)$_k$—Y—

$R_7$—(C($R_6$)$_2$)$_g$—Y—, $R_7$—(C($R_6$)$_2$)$_p$—M—(C($R_6$)$_2$)$_k$—Y—, or Het-(C($R_6$)$_2$)$_q$—W—(C($R_6$)$_2$)$_k$—Y—,

Y is a divalent radical selected from the group consisting of

—S—, —(CH$_2$)$_a$—, —O—, and

—N($R_6$)—;

$R_7$ is —N$R_6R_6$, —O$R_6$, —J, —N($R_6$)$_3$ $^+$Q$^-$, or —N$R_6$(O$R_6$);

M is >N$R_6$, —O—, >N—(C($R_6$)$_2$)$_p$N$R_6R_6$, or >N—(C($R_6$)$_2$)$_p$—O$R_6$;

W is >N$R_6$, —O— or is a bond;

Het is a heterocyclic radical selected from the group consisting of pyrrolidine, aziridine, imidazole, 1,2,3-triazole, 1,2,4-triazole, thiazole, thiazolidine, tetrazole, furan, thiophene, tetrahydrothiophene, tetrahydrofuran, and

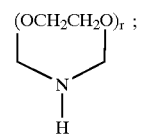

which may be optionally mono- or di-substituted on carbon with $R_6$, hydroxy, —N($R_6$)$_2$, —O$R_6$, —(C($R_6$)$_2$)$_s$O$R_6$ or —(C($R_6$)$_2$)$_s$N($R_6$)$_2$;

optionally mono-substituted on nitrogen with $R_6$; and
optionally mono or di-substituted on a saturated carbon with divalent radicals —O— or —O(C($R_6$)$_2$)$_s$O—;

$R_6$ is hydrogen, alkyl of 1 to 6 carbon atoms, alkenyl of 2 to 6 carbon atoms, alkynyl of 2 to 6 carbon atoms, cycloalkyl of 3 to 7 carbon atoms, carboalkyl of 2 to 7 carbon atoms, carboxyalkyl 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms (alkyl$C_1$–$C_6$) S—, hydroxy, carboxyl, carboalkoxy of 2 to 7 carbon atoms, phenoxy, phenyl, thiophenoxy ($C_6H_5S$—), benzoyl, benzyl, phenylamino, benzylamino, alkanoylamino of 1 to 6 carbon atoms, or alkyl of 1 to 6 carbon atoms; provided that the alkenyl or alkynyl moiety is bound to a nitrogen or oxygen atom through a saturated carbon atom;

$R_2$, is selected from the group consisting of

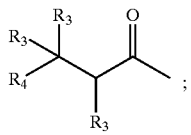

$R_3$ is hydrogen, alkyl of 1 to 6 carbon atoms, carboxy, carboalkoxy of 1 to 6 carbon atoms, phenyl, carboalkyl of 2 to 7 carbon atoms,

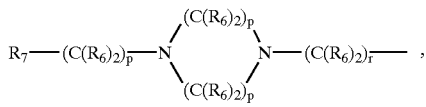

$R_7$—(C($R_6$)$_2$)$_s$—, $R_7$—(C($R_6$)$_2$)$_p$—M—(C($R_6$)$_2$)$_r$—, $R_8R_9$—CH—M—(C($R_6$)$_2$)$_r$—, or Het-(C($R_6$)$_2$)$_q$—W—(C($R_6$)$_2$)$_r$—;

$R_4$ is —$NR_6R_6$, —$OR_6$, —$SR_6$, $R_7$—(C($R_6$)$_2$)$_p$—S—, $R_7$—(C($R_6$)$_2$)$_p$—N($R_6$)—, $R_7$—(C($R_6$)$_2$)$_p$—O—, $R_8R_9$—CH—N($R_6$)—, $R_8R_9$—CH—S—, $R_8R_9$—CH—O—, Het-(C($R_6$)$_2$)$_q$—N($R_6$)—, Het-(C($R_6$)$_2$)$_q$—S—, Het-(C($R_6$)$_2$)$_q$—O—,

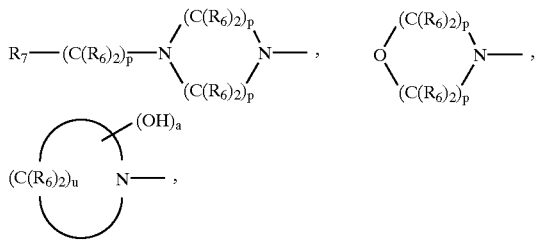

cysteine, or a peptide comprised of 2 to 10 native amino acid residues containing at least one unoxidized cysteine residue wherein $R_4$ is bound to the rest of the molecule through the sulfur atom of one or more of the cysteine residues;

$R_8$ and $R_9$ are each, independently, —(C($R_6$)$_2$)$_r$$NR_6R_6$, or —(C($R_6$)2)$_r$$OR_6$;

J is independently hydrogen, chlorine, fluorine, or bromine;

a is an integer of 0–1;
g is an integer of 1–6;
k is an integer of 0–4;
n is an integer of 0–1;
m is an integer of 0–3;
p is an integer of 2–4;
q is an integer of 0–4;
r is an integer of 1–4;
s is an integer of 1–6
u is an integer of 2–6;

$Q^-$ is a counterion selected from salts formed from organic and inorganic acids;

provided that:
a. when $R_6$ is alkenyl of 2 to 7 carbon atoms or alkynyl of 2 to 7 carbon atoms, such alkenyl or alkynyl moiety is bound to a nitrogen or oxygen atom through a saturated carbon atom;
b. when Y is —$NR_6$— and $R_7$ is —$NR_6R_6$, —N($R_6$)$_3$$^+Q^-$ or —$NR_6$(O$R_6$), then g is an integer of 2 to 6;
c. when M is —O— and $R_7$ is —$OR_6$ then p is an integer of 1 to 4;
d. when Y is —$NR_6$— then k is an integer of 2 to 4;
e. when Y is —O— and M or W is —O— then k is an integer of 1 to 4;
f. when W is not a bond with Het bonded through a nitrogen atom then q is an integer of 2 to 4 and when W is a bond with Het bonded through a nitrogen atom and Y is —O— or —$NR_6$— then k is an integer of 2 to 4;

or a pharmaceutically acceptable salt thereof.

17. A method of treating colonic polyps in a mammal in need thereof which comprises administering to said mammal an effective amount of a compound of Formula (I) represented by the structure:

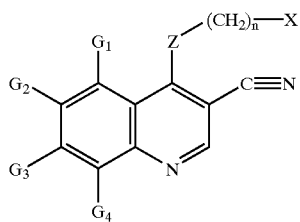

wherein:
Z is —NH—;
X is a phenyl which may optionally be mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or X is the radical

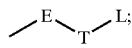

E is a phenyl optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

T is substituted on E at carbon and is
—NH($CH_2$)$_m$—, —O($CH_2$)$_m$—, —S($CH_2$)$_m$—, —NR($CH_2$)$_m$—, —($CH_2$)$_m$—
—($CH_2$)$_m$NH—, —($CH_2$)$_m$O—, —($CH_2$)$_m$S—, or —($CH_2$)$_m$NR—;

L is an aryl ring optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy ($C_6H_5$S—), benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

Pyridinyl, pyrimidinyl, or aryl are pyridinyl, pyrimidinyl, or aryl radicals, respectively, optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

$G_3$ is an alkoxy of 1 to 6 carbon atoms;

$G_2$ is $R_2$NH—;

$G_1$, and $G_4$ are each, independently, hydrogen, halogen, alkyl of 1 to 6 carbon atoms, alkenyl of 2 to 6 carbon atoms, alkynyl of 2 to 6 carbon atoms, alkenyloxy of 2 to 6 carbon atoms, alkynyloxy of 2 to 6 carbon atoms, hydroxymethyl, halomethyl, alkanoyloxy of 2 to 8 carbon atoms, alkenoyloxy of 3 to 8 carbon atoms, alkynoyloxy of 3 to B carbon atoms, alkanoyloxymethyl of 2 to 7 carbon atoms, alkenoyloxymethyl of 4 to 9 carbon atoms, alkynoyloxymethyl of 4 to 9 carbon atoms, alkoxymethyl of 2 to 7 carbon atoms, alkoxy of 1 to 6 carbon atoms, alkylthio of 1 to 6 carbon atoms (alkyl$C_1$–$C_6$)S—, alkylsulphinyl of 1 to 6 carbon atoms, alkylsulphonyl of 1 to 6 carbon atoms, alkylsulfonamido of 1 to 6 carbon atoms, alkenylsulfonamido of 2 to 6 carbon atoms, alkynylsulfonamido of 2 to 6 carbon atoms, hydroxy, trifluoromethyl, trifluoromethoxy, cyano, nitro, carboxy, carboalkoxy of 2 to 7 carbon atoms, carboalkyl of 2 to 7 carbon atoms, phenoxy, phenyl, thiophenoxy ($C_6H_5$S—), benzyl, amino, hydroxyamino, alkoxyamino of 1 to 4 carbon atoms, alkylamino of 1 to 6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6 to 12 carbon atoms, phenylamino, benzylamino, R₂NH,

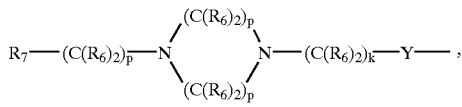

$R_8R_9$—CH—M—$(C(R_6)_2)_k$—Y—

$R_7$—$(C(R_6)_2)_g$—Y—, $R_7$—$(C(R_6)_2)_p$—M—$(C(R_6)_2)_k$—Y—, or Het-$(C(R_6)_2)_q$—W—$(C(R_6)_2)_k$—Y—,

Y is a divalent radical selected from the group consisting of

—S—, —(CH₂)ₐ—, —O—, and

—N(R₆)—;

R₇ is —NR₆R₆, —OR₆, —J, —N(R₆)₃ ⁺Q⁻, or —NR₆(OR₆);

M is >NR₆, —O—, >N—$(C(R_6)_2)_p$NR₆R₆, or >N—$(C(R_6)_2)_p$—OR₆;

W is >NR₆, —O— or is a bond;

Het is a heterocyclic radical selected from the group consisting of pyrrolidine, aziridine, imidazole, 1,2,3-triazole, 1,2,4-triazole, thiazole, thiazolidine, tetrazole, furan, thiophene, tetrahydrothiophene, tetrahydrofuran, and

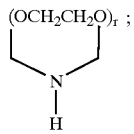

which may be optionally mono- or di-substituted on carbon with R₆, hydroxy, —N(R₆)₂, —OR₆, —$(C(R_6)_2)_s$OR₆ or —$(C(R_6)_2)_s$N(R₆)₂;

optionally mono-substituted on nitrogen with R₆; and optionally mono or di-substituted on a saturated carbon with divalent radicals —O— or —O$(C(R_6)_2)_s$O—;

R₆ is hydrogen, alkyl of 1 to 6 carbon atoms, alkenyl of 2 to 6 carbon atoms, alkynyl of 2 to 6 carbon atoms, cycloalkyl of 3 to 7 carbon atoms, carboalkyl of 2 to 7 carbon atoms, carboxyalkyl 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms (alkylC₁–C₆)S—, hydroxy, carboxyl, carboalkoxy of 2 to 7 carbon atoms, phenoxy, phenyl, thiophenoxy (C₆H₅S—), benzoyl, benzyl, phenylamino, benzylamino, alkanoylamino of 1 to 6 carbon atoms, or alkyl of 1 to 6 carbon atoms; provided that the alkenyl or alkynyl moiety is bound to a nitrogen or oxygen atom through a saturated carbon atom;

R₂, is selected from the group consisting of

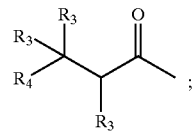

R₃ is hydrogen, alkyl of 1 to 6 carbon atoms, carboxy, carboalkoxy of 1 to 6 carbon atoms, phenyl, carboalkyl of 2 to 7 carbon atoms,

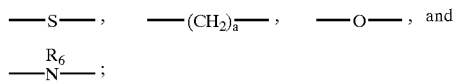

$R_7$—$(C(R_6)_2)_s$—, $R_7$—$(C(R_6)_2)_p$—M—$C(R_6)_2)_r$—,
$R_8R_9$—CH—M—$(C(R_6)_2)_r$—, or Het-$(C(R_6)_2)_q$—W—$(C(R_6)_2)_r$—;

R₄ is —NR₆R₆, —OR₆, —SR₆,
$R_7$—$(C(R_6)_2)_p$—S—, $R_7$—$(C(R_6)_2)_p$—N(R₆)—, $R_7$—$(C(R_6)_2)_p$—O—,
$R_8R_9$—CH—N(R₆)—, $R_8R_9$—CH—S—, $R_8R_9$—CH—O—,
Het-$(C(R_6)_2)_q$—N(R₆)—, Het-$(C(R_6)_2)_q$—S—, Het-$(C(R_6)_2)_q$—O—,

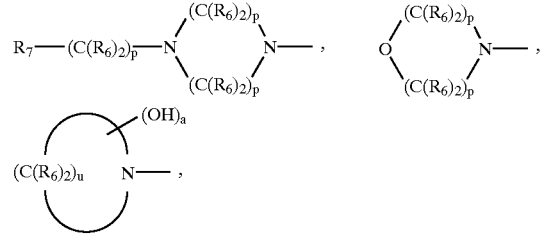

cysteine, or a peptide comprised of 2 to 10 native amino acid residues containing at least one unoxidized cysteine residue wherein R₄ is bound to the rest of the molecule through the sulfur atom of one or more of the cysteine residues;

R₈ and R₉ are each, independently, —$(C(R_6)_2)_r$NR₆R₆, or —$(C(R_6)2)_r$OR₆;

J is independently hydrogen, chlorine, fluorine, or bromine;

a is an integer of 0–1;
g is an integer of 1–6;
k is an integer of 0–4;
n is an integer of 0–1;
m is an integer of 0–3;
p is an integer of 2–4;
q is an integer of 0–4;
r is an integer of 1–4;
s is an integer of 1–6
u is an integer of 2–6;

Q⁻ is a counterion selected from salts formed from organic and inorganic acids;

provided that:
a. when R₆ is alkenyl of 2 to 7 carbon atoms or alkynyl of 2 to 7 carbon atoms, such alkenyl or alkynyl moiety is bound to a nitrogen or oxygen atom through a saturated carbon atom;

b. when Y is —NR$_6$— and R$_7$ is —NR$_6$R$_6$, —N(R$_6$)$_3$$^+$Q$^-$, or —NR$_6$(OR$_6$), then g is an integer of 2 to 6;
c. when M is —O— and R$_7$ is —OR$_6$ then p is an integer of 1 to 4;
d. when Y is —NR$_6$— then k is an integer of 2 to 4;
e. when Y is —O— and M or W is —O— then k is an integer of 1 to 4;
f. when W is not a bond with Het bonded through a nitrogen atom then q is an integer of 2 to 4 and when W is a bond with Het bonded through a nitrogen atom and Y is —O— or —NR$_6$— then k is an integer of 2 to 4;

or a pharmaceutically acceptable salt thereof.

18. A pharmaceutical composition which comprises a compound of Formula (I) represented by the structure

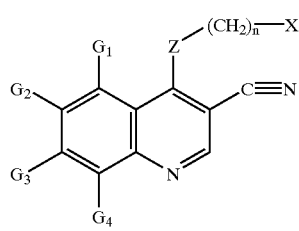

wherein:

Z is —NH—;

X is a phenyl which may optionally be mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkylC$_1$–C$_8$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or X is the radical

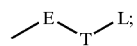

E is a phenyl optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkylC$_1$–C$_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

T is substituted on E at carbon and is
—NH(OH$_2$)$_m$—, —O(CH$_2$)$_m$—, —S(CH$_2$)$_m$—, —NR(CH$_2$)$_m$—, —(CH$_2$)$_m$—
—(CH$_2$)$_m$NH—, —(CH$_2$)$_m$O—, —(CH$_2$)$_m$S—, or —(CH$_2$)$_m$NR—;

L is an aryl ring optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkylC$_1$–C$_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino; or L is a 5- or 6-membered heteroaryl ring where the heteroaryl ring contains 1 to 3 heteroatoms independently selected from N, O, and S; wherein the heteroaryl ring may be optionally mono- or di-substituted with a substituent selected from the group consisting of halogen, oxo, thio, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkylC$_1$–C$_6$)S—, hydroxy, trifluoromethyl, cyano, nitro, carboxy, carboalkoxy of 2 to 7 carbon atoms, carboalkyl of 2 to 7 carbon atoms, phenoxy, phenyl, thiophenoxy (C$_6$H$_5$S—), benzoyl, benzyl, amino, alkylamino of 1 to 6 carbon atoms, dialkylamino of 2 to 12 carbon atoms, phenylamino, benzylamino, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1 to 5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

Pyridinyl, pyrimidinyl, or aryl are pyridinyl, pyrimidinyl, or aryl radicals, respectively, optionally mono- di-, or tri-substituted with a substituent selected from the group consisting of halogen, alkyl of 1 to 6 carbon atoms, alkenyl of 2 to 6 carbon atoms, alkynyl of 2 to 6 carbon atoms, azido, hydroxyalkyl of 1 to 6 carbon atoms, halomethyl, alkoxymethyl of 2 to 7 carbon atoms, alkanoyloxymethyl of 2 to 7 carbon atoms, alkoxy of 1 to 6 carbon atoms, alkylthio of 1 to 6 carbon atoms (alkyl$C_1$–$C_6$)S—, hydroxy, trifluoromethyl, cyano, nitro, carboxy, carboalkoxy of 2 to 7 carbon atoms, carboalkyl of 2 to 7 carbon atoms, benzoyl, amino, alkylamino of 1 to 6 carbon atoms, dialkylamino of 2 to 12 carbon atoms, alkanoylamino of 1 to 6 carbon atoms, alkenoylamino of 3 to 8 carbon atoms, alkynoylamino of 3 to 8 carbon atoms, carboxyalkyl of 2 to 7 carbon atoms, carboalkoxyalkyl of 3 to 8 carbon atoms, aminoalkyl of 1–5 carbon atoms, N-alkylaminoalkyl of 2 to 9 carbon atoms, N,N-dialkylaminoalkyl of 3 to 10 carbon atoms, N-alkylaminoalkoxy of 2 to 9 carbon atoms, N,N-dialkylaminoalkoxy of 3 to 10 carbon atoms, mercapto, and benzylamino;

$G_3$ is an alkoxy of 1 to 6 carbon atoms;

$G_2$ is $R_2NH$—;

$G_1$, and $G_4$ are each, independently, hydrogen, halogen, alkyl of 1 to 6 carbon atoms, alkenyl of 2 to 6 carbon atoms, alkynyl of 2 to 6 carbon atoms, alkenyloxy of 2 to 6 carbon atoms, alkynyloxy of 2 to 6 carbon atoms, hydroxymethyl, halomethyl, alkanoyloxy of 2 to 6 carbon atoms, alkenoyloxy of 3 to 8 carbon atoms, alkynoyloxy of 3 to 8 carbon atoms, alkanoyloxymethyl of 2 to 7 carbon atoms, alkenoyloxymethyl of 4 to 9 carbon atoms, alkynoyloxymethyl of 4 to 9 carbon atoms, alkoxymethyl of 2 to 7 carbon atoms, alkoxy of 1 to 6 carbon atoms, alkylthio of 1 to 6 carbon atoms (alkyl$C_1$–$C_6$)S—, alkylsulphinyl of 1 to 6 carbon atoms, alkylsulphonyl of 1 to 6 carbon atoms, alkylsulfonamido of 1 to 6 carbon atoms, alkenylsulfonamido of 2 to 6 carbon atoms, alkynylsulfonamido of 2 to 6 carbon atoms, hydroxy, trifluoromethyl, trifluoromethoxy, cyano, nitro, carboxy, carboalkoxy of 2 to 7 carbon atoms, carboalkyl of 2 to 7 carbon atoms, phenoxy, phenyl, thiophenoxy ($C_6H_5S$—), benzyl, amino, hydroxyamino, alkoxyamino of 1 to 4 carbon atoms, alkylamino of 1 to 6 carbon atoms, dialkylamino of 2 to 12 carbon atoms, N-alkylcarbamoyl, N,N-dialkylcarbamoyl, N-alkyl-N-alkenylamino of 4 to 12 carbon atoms, N,N-dialkenylamino of 6 to 12 carbon atoms, phenylamino, benzylamino, $R_2NH$,

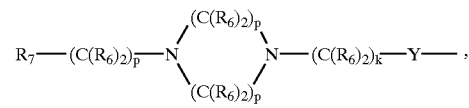

$R_8R_9$—CH—M—(C($R_6$)$_2$)$_k$—Y—
$R_7$—(C($R_6$)$_2$)$_g$—Y—, $R_7$—(C($R_6$)$_2$)$_p$—M—(C($R_6$)$_2$)$_k$—Y—, or Het-(C($R_6$)$_2$)$_q$—W—(C($R_6$)$_2$)$_k$—Y—,

Y is a divalent radical selected from the group consisting of

—S—, —(CH$_2$)$_a$—, —O—, and
—$\underset{R_6}{N}$—;

$R_7$ is —NR$_6$R$_6$, —OR$_6$, —J, —N(R$_6$)$_3$ $^+$Q$^-$, or —NR$_6$(OR$_6$);

M is >NR$_6$, —O—, >N—(C(R$_6$)$_2$)$_p$NR$_6$R$_6$, or >N—(C(R$_6$)$_2$)$_p$—OR$_6$;

W is >NR$_6$, —O— or is a bond;

Het is a heterocyclic radical selected from the group consisting of pyrrolidine, aziridine, imidazole, 1,2,3-triazole, 1,2,4-triazole, thiazole, thiazolidine, tetrazole, furan, thiophene, tetrahydrothiophene, tetrahydrofuran, and

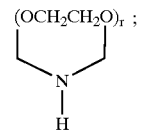

which may be optionally mono- or di-substituted on carbon with R$_6$, hydroxy, —N(R$_6$)$_2$, —OR$_6$, —(C(R$_6$)$_2$)$_s$OR$_6$ or —(C(R$_6$)$_2$)$_s$N(R$_6$)$_2$;

optionally mono-substituted on nitrogen with R$_6$; and optionally mono or di-substituted on a saturated carbon with divalent radicals —O— or —O(C(R$_6$)$_2$)$_s$O—;

R$_6$ is hydrogen, alkyl of 1 to 6 carbon atoms, alkenyl of 2 to 6 carbon atoms, alkynyl of 2 to 6 carbon atoms, cycloalkyl of 3 to 7 carbon atoms, carboalkyl of 2 to 7 carbon atoms, carboxyalkyl 2 to 7 carbon atoms, phenyl, or phenyl optionally substituted with one or more halogen, alkoxy of 1 to 6 carbon atoms, trifluoromethyl, amino, alkylamino of 1 to 3 carbon atoms, dialkylamino of 2 to 6 carbon atoms, nitro, cyano, azido, halomethyl, alkoxymethyl of 2 to 7 carbon atoms, alkanoyloxymethyl of 2 to 7 carbon atoms, alkylthio of 1 to 6 carbon atoms (alkyl$C_1$–$C_6$)S—, hydroxy, carboxyl, carboalkoxy of 2 to 7 carbon atoms, phenoxy, phenyl, thiophenoxy ($C_6H_5S$—), benzoyl, benzyl, phenylamino, benzylamino, alkanoylamino of 1 to 6 carbon atoms, or alkyl of 1 to 6 carbon atoms; provided that the alkenyl or alkynyl moiety is bound to a nitrogen or oxygen atom through a saturated carbon atom;

R$_2$, is selected from the group consisting of

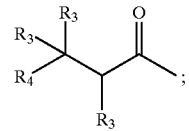

R$_3$ is hydrogen, alkyl of 1 to 6 carbon atoms, carboxy, carboalkoxy of 1 to 6 carbon atoms, phenyl, carboalkyl of 2 to 7 carbon atoms,

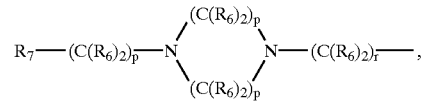

$R_7$—(C($R_6$)$_2$)$_s$—, $R_7$—(C($R_6$)$_2$)$_p$—M—C($R_6$)$_2$)$_r$—,
$R_8R_9$—CH—M—(C($R_6$)$_2$)$_r$—, or Het-(C($R_6$)$_2$)$_q$—W—(C($R_6$)$_2$)$_r$—;

R$_4$ is —NR$_6$R$_6$, —OR$_6$, —SR$_6$,
$R_7$—(C($R_6$)$_2$)$_p$—S—, $R_7$—(C($R_6$)$_2$)$_p$—N(R$_6$)—, $R_7$—(C($R_6$)$_2$)$_p$—O—,
$R_8R_9$—CH—N(R$_6$)—, $R_8R_9$—CH—S—, $R_8R_9$—CH—O—,
Het-(C($R_6$)$_2$)$_q$—N(R$_6$)—, Het-(C($R_6$)$_2$)$_q$—S—, Het-(C($R_6$)$_2$)$_q$—O—,

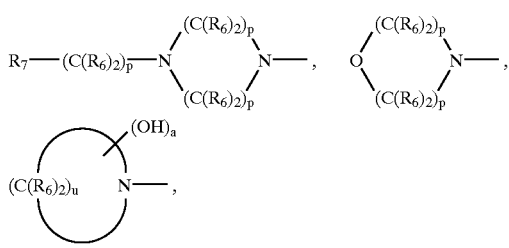

cysteine, or a peptide comprised of 2 to 10 native amino acid residues containing at least one unoxidized cysteine residue wherein $R_4$ is bound to the rest of the molecule through the sulfur atom of one or more of the cysteine residues;

$R_8$ and $R_9$ are each, independently, —$(C(R_6)_2)_r NR_6 R_6$, or —$(C(R_6)2)_r OR_6$;

J is independently hydrogen, chlorine, fluorine, or bromine;

a is an integer of 0–1;

g is an integer of 1–6;

k is an integer of 0–4;

n is an integer of 0–1;

m is an integer of 0–3;

p is an integer of 2–4;

q is an integer of 0–4;

r is an integer of 1–4;

s is an integer of 1–6 u is an integer of 2–6;

$Q^-$ is a counterion selected from salts formed from organic and inorganic acids;

provided that:

a. when $R_6$ is alkenyl of 2 to 7 carbon atoms or alkynyl of 2 to 7 carbon atoms, such alkenyl or alkynyl moiety is bound to a nitrogen or oxygen atom through a saturated carbon atom;

b. when Y is —$NR_6$— and $R_7$ is —$NR_6 R_6$, —$N(R_6)_3$ $^+Q^-$, or —$NR_6(OR_6)$, then g is an integer of 2 to 6;

c. when M is —O— and $R_7$ is —$OR_6$ then p is an integer of 1 to 4;

d. when Y is —$NR_6$— then k is an integer of 2 to 4;

e. when Y is —O— and M or W is —O— then k is an integer of 1 to 4;

f. when W is not a bond with Het bonded through a nitrogen atom then q is an integer of 2 to 4 and when W is a bond with Het bonded through a nitrogen atom and Y is —O— or —$NR_6$— then k is an integer of 2 to 4;

or a pharmaceutically acceptable salt thereof in association with one or more pharmaceutically acceptable carriers.

19. The compound according to claim 1, which is N-{4-[4-(Benzyloxy)-3-chloroanilino]-3-cyano-7-ethoxy-6-quinolinyl}-3,4-bis(dimethylamino)butanamide or a pharmaceutically acceptable salt thereof.

* * * * *

UNITED STATES PATENT AND TRADEMARK OFFICE
CERTIFICATE OF CORRECTION

PATENT NO. : 6,821,988 B2
DATED : November 23, 2004
INVENTOR(S) : Allan Wissner et al.

It is certified that error appears in the above-identified patent and that said Letters Patent is hereby corrected as shown below:

Column 36,
Line 64, replace "$–NH(OH_2)_m–$" with -- $–NH(CH_2)_m–$ --

Column 42,
Line 49, replace "2 to 8" with -- 2 to 6 --
Line 51, replace "3 to B" with -- 3 to 8 --

Column 45,
Line 37, replace "$(alkylC_1-C_8)S-$" with -- $(alkylC_1-C_6)S-$ --

Column 46,
Line 12, replace "$–NH(OH_2)_m-$" with -- $–NH(CH_2)_m–$ --

Signed and Sealed this

Nineteenth Day of April, 2005

JON W. DUDAS
*Director of the United States Patent and Trademark Office*